US011578354B2

(12) United States Patent
Sinha et al.

(10) Patent No.: US 11,578,354 B2
(45) Date of Patent: Feb. 14, 2023

(54) METHODS AND DEVICES FOR SINGLE-CELL BASED DIGITAL HIGH RESOLUTION MELT

(71) Applicant: MelioLabs Inc., Santa Clara, CA (US)

(72) Inventors: Mridu Sinha, Santa Clara, CA (US); Ryan Simkovsky, Santa Clara, CA (US); Kaushik Sridhar, Santa Clara, CA (US); Shubhodeep Paul, Santa Clara, CA (US); Amol Chaudhary, Santa Clara, CA (US)

(73) Assignee: MELIOLABS INC., Santa Clara, CA (US)

( * ) Notice: Subject to any disclaimer, the term of this patent is extended or adjusted under 35 U.S.C. 154(b) by 141 days.

(21) Appl. No.: 17/023,362

(22) Filed: Sep. 16, 2020

(65) Prior Publication Data
US 2021/0214768 A1    Jul. 15, 2021

Related U.S. Application Data

(60) Provisional application No. 62/874,543, filed on Jul. 16, 2019.

(51) Int. Cl.
*C12Q 1/6806* (2018.01)
*C12Q 1/686* (2018.01)
*C12Q 1/06* (2006.01)

(52) U.S. Cl.
CPC ............. *C12Q 1/6806* (2013.01); *C12Q 1/06* (2013.01); *C12Q 1/686* (2013.01)

(58) Field of Classification Search
None
See application file for complete search history.

(56) References Cited

U.S. PATENT DOCUMENTS

| 10,093,989 B2* | 10/2018 | Chelliserry | .......... C12Q 1/6806 |
| 10,513,733 B2* | 12/2019 | Georgiou | ............. C12Q 1/6804 |
| 11,098,342 B2* | 8/2021 | Simon | .................. C12Q 1/6806 |
| 2003/0143587 A1* | 7/2003 | Dean | ................ C12Q 2525/125 |
| | | | 435/6.1 |
| 2003/0215845 A1* | 11/2003 | Bille | .................. C12N 15/1017 |
| | | | 435/6.12 |
| 2003/0228613 A1* | 12/2003 | Bornarth | ............. C12Q 1/6844 |
| | | | 435/6.12 |

(Continued)

OTHER PUBLICATIONS

Baker, M. Digital PCR hits its stride. *Nat Meth* 9, 541-544 (2012).

(Continued)

*Primary Examiner* — Brian R Gordon
(74) *Attorney, Agent, or Firm* — Knobbe, Martens, Olson & Bear LLP

(57) ABSTRACT

Provided are devices, systems, and methods for the identification, quantification, and profiling of microscopic organisms. The methods for the identification, quantification, and profiling of microscopic organisms include, for example, the selective enrichment of microscopic organisms from a heterogeneous sample; subsequent loading of the microscopic organisms into microfluidic channels or reaction chambers; direct amplification of nucleic acids from single, isolated microscopic organisms; and examination of amplification products using digital High Resolution Melting (HRM) analysis.

20 Claims, 11 Drawing Sheets

(56) References Cited

U.S. PATENT DOCUMENTS

| | | | | |
|---|---|---|---|---|
| 2004/0265864 | A1* | 12/2004 | Mitsuhashi | C12Q 1/6846 435/6.18 |
| 2005/0053942 | A1* | 3/2005 | Kauppinen | C12N 15/1006 435/6.12 |
| 2008/0044864 | A1* | 2/2008 | Jeong | B01L 7/52 435/91.2 |
| 2008/0176320 | A1* | 7/2008 | Liu | C12Q 1/6806 435/325 |
| 2008/0187924 | A1* | 8/2008 | Korfhage | C12Q 1/6806 435/6.1 |
| 2009/0062140 | A1* | 3/2009 | Gilbert | C12Q 1/6804 506/9 |
| 2010/0179310 | A1* | 7/2010 | Kamme | C12Q 1/6806 536/25.41 |
| 2011/0005932 | A1* | 1/2011 | Jovanovich | G01N 27/44721 204/453 |
| 2011/0027771 | A1* | 2/2011 | Deng | C12Q 1/6806 435/2 |
| 2012/0322058 | A1* | 12/2012 | Regan | C12Q 1/6883 435/6.11 |
| 2013/0059762 | A1* | 3/2013 | Leamon | C12Q 1/6806 506/26 |
| 2013/0078641 | A1* | 3/2013 | Viljoen | C12Q 1/6806 435/6.12 |
| 2013/0109590 | A1* | 5/2013 | Clarizia | G01N 33/56911 506/9 |
| 2013/0130265 | A1* | 5/2013 | Parikh | G01N 33/5005 435/6.12 |
| 2013/0273640 | A1* | 10/2013 | Krishnan | B01D 57/02 435/270 |
| 2013/0296535 | A1* | 11/2013 | Church | G16B 20/00 530/387.1 |
| 2014/0295419 | A1* | 10/2014 | Zhang | C12Q 1/6865 435/6.11 |
| 2015/0038855 | A1* | 2/2015 | Berckmans | A61B 5/18 600/483 |
| 2015/0045237 | A1* | 2/2015 | Landthaler | C12Q 1/6804 506/4 |
| 2015/0079601 | A1* | 3/2015 | Slepnev | C12Q 1/6806 435/6.12 |
| 2015/0105287 | A1* | 4/2015 | Lu | G01N 33/54326 506/9 |
| 2015/0133319 | A1* | 5/2015 | Fu | C12Q 1/6806 506/4 |
| 2015/0141261 | A1* | 5/2015 | Hunicke-Smith | C12Q 1/6806 506/2 |
| 2015/0299770 | A1* | 10/2015 | Tatnell | C12N 15/1006 435/91.2 |
| 2016/0017315 | A1* | 1/2016 | Kenrick | C12Q 1/6848 435/91.21 |
| 2016/0068897 | A1* | 3/2016 | Talebpour | C12Q 1/6806 506/12 |
| 2016/0230153 | A1* | 8/2016 | Reichert | C12N 9/1252 |
| 2017/0121756 | A1* | 5/2017 | Abate | C12Q 1/6886 |
| 2017/0130219 | A1* | 5/2017 | Birnboim | C12N 1/06 |
| 2017/0166956 | A1* | 6/2017 | Driscoll | C12Q 1/6874 |
| 2017/0211129 | A1* | 7/2017 | Suh | B01D 15/125 |
| 2017/0283859 | A1* | 10/2017 | Lin | B01L 3/502761 |
| 2017/0321257 | A1* | 11/2017 | Andini | C12Q 1/6816 |
| 2018/0142231 | A1* | 5/2018 | Kubicek | C12N 15/1003 |
| 2018/0208975 | A1* | 7/2018 | Peterson | C12Q 1/6851 |
| 2018/0230451 | A1* | 8/2018 | Selden | C12Q 1/6806 |
| 2018/0237951 | A1* | 8/2018 | Bock | C12Q 1/6806 |
| 2018/0282786 | A1* | 10/2018 | Pugia | C12Q 1/6806 |
| 2018/0305685 | A1* | 10/2018 | Li | C12Q 1/6806 |
| 2018/0305735 | A1* | 10/2018 | Fiss | C12Q 1/6888 |
| 2019/0187031 | A1* | 6/2019 | Johnson-Buck | C12Q 1/6816 |
| 2019/0345538 | A1* | 11/2019 | Jasper | C12Q 1/686 |
| 2021/0189379 | A1* | 6/2021 | Ismagilov | C12N 15/1006 |
| 2021/0214798 | A1* | 7/2021 | Krishnan | C12Q 1/6883 |
| 2021/0241857 | A1* | 8/2021 | Fraley | C12Q 1/686 |
| 2021/0261953 | A1* | 8/2021 | Fordyce | C12Q 1/6806 |

OTHER PUBLICATIONS

Bhat, S., Herrmann, J., Armishaw, P., Corbisier, P. & Emslie, K. R. Single molecule detection in nanofluidic digital array enables accurate measurement of DNA copy number *Anal. Bioanal. Chem.*. 394, 457-467 (2009).

Boardman, A. K., Campbell, J., Wirz, H., Sharon, A. & Sauer-Budge, A. F. Rapid microbial sample preparation from blood using a novel concentration device. *PLoS One 10*, e0116837 (2015).

Dietzman, D. E., Fischer, G. W. & Schoenknecht, F. D. Neonatal *Escherichia coli* septicemia—bacterial counts in blood. *J. Pediatr.* 85, 128-130 (1974).

Dube, S., Qin, J. & Ramakrishnan, R. Mathematical analysis of copy number variation in a DNA sample using digital PCR on a nanofluidic device. *PLoS One* 3, e2876 (2008).

Frey, K. G. et al. Comparison of three next-generation sequencing platforms for metagenomic sequencing and identification of pathogens in blood. *BMC Genomics* 15, 96 (2014).

Gole, J. et al. Massively parallel polymerase cloning and genome sequencing of single cells using nanoliter microwells. *Nat. Biotechnol.* 31, 1126-1132 (2013).

Hindson, B. J. et al. High-throughput droplet digital PCR system for absolute quantitation of DNA copy number *Anal. Chem.* 83, 8604-8610 (2011).

Kellogg, J. A. et al. Frequency of low level bacteremia in infants from birth to two months of age. *Pediatr. Infect. Dis. J.* 16, 381-5 (1997).

Malentacchi, F. et al. Influence of pre-analytical procedures on genomic DNA integrity in blood samples: The SPIDIA experience. *Clin. Chim. Acta* 440, 205-210 (2015).

Prachayangprecha, S. et al. Exploring the Potential of Next-Generation Sequencing in Detection of Respiratory Viruses. *J. Clin. Microbiol.* 52, 3722-3730 (2014).

Sedlak, R. H. & Jerome, K. R. Viral diagnostics in the era of digital polymerase chain reaction. *Diagn. Microbiol. Infect. Dis.* 75, 1-4 (2013).

Sinha, M. et al. Emerging Technologies for Molecular Diagnosis of Sepsis. *Clin. Microbiol. Rev.* 31, e00089-17 (2018).

Sinha, M., Mack, H., Coleman, T. P. & Fraley, S. I. A High-Resolution Digital DNA Melting Platform for Robust Sequence Profiling and Enhanced Genotype Discrimination. *SLAS Technol. Transl. Life Sci. Innov.* 247263031876984 (2018). doi:10.1177/2472630318769846.

Velez, D. O. et al. Massively parallel digital high resolution melt for rapid and absolutely quantitative sequence profiling. *Sci. Rep.* 7, 42326 (2017).

Vogelstein, B. & Kinzler, K. W. Digital Pcr. *Proc. Natl. Acad. Sci.* 96, 9236-9241 (1999).

\* cited by examiner

= *E. Coli* expressing GFP
= *E. Coli* expressing RFP & β-lactamase
 β-lactamase activity sensor

METHODS AND DEVICES FOR SINGLE-CELL BASED DIGITAL HIGH RESOLUTION MELT

CROSS-REFERENCES TO RELATED APPLICATIONS

The present application is related to U.S. Provisional Pat. Appl. No. 62/874,543, filed Jul. 16, 2019, the teachings of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention provides devices, systems, and methods for the identification, quantification, and profiling of a microscopic organism, i.e., a microorganism, which involve the selective enrichment of the microscopic organism from a heterogeneous sample; subsequent compartmentalization of the microscopic organisms into a plurality (or array) of reaction chambers; lysis of the microscopic organism to release nucleic acid, subsequent amplification of a target nucleic acid from each reaction chamber; and examination of the amplification products using High Resolution Melting (HRM) analysis.

BACKGROUND OF THE INVENTION

Profiling and quantification of complex samples for low-level genotypes in a rapid and accurate manner represents a significant challenge for microbial detection applications, including, but not limited to, clinical diagnostics, pathogen or contamination detection, bio-threat assessments, and evaluation of environmental and human-based microbiomes. Advances in speed, sensitivity, accuracy, and extent of multiplexing for multiple groupings of organisms are needed to improve molecular pathogen detection assays that improve patient care, enable cutting edge scientific research, and keep populations safe from potential biological hazards.

High resolution melt or, alternatively, HRM refer to a technique for determining a sequence variation in a nucleic acid by analyzing a melting curve of the nucleic acid sequence. The HRM process in its simplest form entails a melting step during which precise control of a heating element allows for the sequence-dependent denaturation of double-stranded DNA (dsDNA) to single stranded DNA (ssDNA).

High resolution melt alone is capable of sequence identification based on fingerprint melt, but it does not provide any quantitative information. Digital PCR (dPCR) is unable to provide quantitative information about mixed samples and is limited by the requirements put in place by the use of TaqMan probes. Although digital High Resolution Melt (dHRM) is capable of identifying and quantifying microbial genomes in a polymicrobial sample, this methodology, like all other PCR-based technologies including both NGS and qPCR-based detection systems, is unable to generate accurate, unbiased cell counts or sample-specific detection results due to organismal differences in genetic ploidy or changes in ploidy during the replication cycle, species-specific biases in the DNA extraction process, the presence of inhibitors in samples such as blood or soil, and the predominance of non-microbial or host DNA that either inhibits the amplification reaction or causes target DNAs to be present below the detection limits of the methodology. Further, these technologies are unable to evaluate, quantitate, and associate antibiotic resistances with specific species present in a sample because they rely upon the need to initially extracting DNA from organisms in the sample in bulk. DNA extraction typically dissociates antibiotic resistance markers from chromosomal species markers due to fragmentation of chromosomal DNA or separation of plasmid-encoded resistance markers from chromosomal DNA. This linkage of information is important, however, because it can further enable identification of multi-resistant organisms and, in turn, the prevalence of resistance in a sample to critically inform treatment and reduce inappropriate use of antibiotics. For example, in a neonatal clinical environment, the knowledge of which species is resistant is critical information that can guide precise targeted clinical care in, for example, vulnerable newborns who have much lower tolerances to antibiotics in comparison to the adult population. Further, DNA extraction can result in accidental exposure to contaminants, fragmentation of DNA and loss of sensitivity can lead to the carryover of agents known to be inhibitors of amplification and HRM analysis that are present in the sample. In the case of RNA, the stability of RNA is of utmost concern if reliable results are to be obtained. In view of these deficiencies in the prior art, there is a need for a system, method, and apparatus that can perform both genus and species-level identification of microbes, perform quantitation of microbial cell populations, and preserve linkage information between multiple genotypic markers to enable cell-based quantitation of these markers.

BRIEF SUMMARY OF THE INVENTION

The present invention provides devices, systems, and methods for the identification and quantification of a microscopic organisms in a sample. In the methods of the present invention, samples or reaction mixtures containing intact microbial cells are partitioned into, for example, 10,000 or greater reaction chambers or wells and subjected to cell lysis in situ (e.g., to release the nucleic acids contained in the microbes into the reaction volume of each partition) so that nucleic acid sequences can be analyzed by amplification and high resolution melt (HRM) analysis. In one aspect, a method for identifying and quantifying microbial cells in a sample is provided, the method comprising: enriching the sample for microbial cells by removing non-microbial cells and nucleic acid from the heterogeneous sample to provide an enriched sample; combining the enriched sample with a master mix to form a reaction mixture, wherein the master mix comprises at least one microbial cell lysis agent and at least one reaction buffer for amplification and HRM analysis; partitioning the reaction mixture into at least 10,000 reaction chambers; lysing the microbial cells in the reaction mixture in each of the reaction chambers to create a lysed sample comprising a nucleic acid; performing amplification of the nucleic acid in the lysed sample in each of the reaction chambers to produce an amplification product, wherein the amplification is simultaneously carried out in each of the reaction chambers; performing dHRM analysis of the amplification products in each of the reaction chambers to capture a melt curve signal, wherein the dHRM analysis is simultaneously carried out in each reaction chamber; and comparing the melt curve in each reaction chamber to a plurality of melt curves from known nucleic acid sequences using computer algorithms, thereby identifying and quantitating the microbial cells in the heterogeneous sample. As used herein, a "heterogeneous sample," which is also referred to herein as "a sample," can comprise of one or more microorganisms, and include non-microbial cells, mammalian cells, and contaminating microbial and mammalian nucleic acid. Using the methods of the present invention, identification, quantification, and profiling of multiple species and even multiple variants within same species organisms can be achieved from a heterogeneous samples, including samples contaminated with the host or other non-target cells, or nucleic acid (DNA and RNA).

In some embodiments, enrichment of the microbial cells is performed following a selective buffer-based lysis step of human and/or non-microbial cells. In a preferred embodiment, the lysing step is carried out simultaneously on each of the reaction chambers. In another preferred embodiment, the amplification step in carried out simultaneously on each of the reaction chambers. In yet another preferred embodiment, the HRM analysis is carried out simultaneously on each of the reaction chambers.

In another aspect, a method for identifying and quantifying microbial cells in a sample is provided that further includes additional phenotypic and genotypic profiling of microbial cells prior to and/or post cell lysis. Such profiling analyses can include, but are not limited to, speciation via cell imaging and determination of resistance. In one such embodiment, a method for identifying and quantifying microbial cells in a sample is provided, the method comprising: enriching the sample for microbial cells by removing non-microbial cells and nucleic acid from the heterogeneous sample to provide an enriched sample; combining the enriched sample with a master mix to form a reaction mixture, wherein the master mix comprises at least one microbial cell lysis agent and at least one reaction buffer for amplification and HRM analysis; partitioning the reaction mixture into at least 10,000 reaction chambers; profiling of the intact microbial cells in each of the reaction chambers using non-dHRM based analysis; lysing the microbial cells in the reaction mixture in each of the reaction chambers to create a lysed sample comprising a nucleic acid; profiling of the lysed sample mixture in each of the reaction chambers using non-dHRM based analysis; performing amplification of the nucleic acid in the lysed sample in each of the reaction chambers to produce an amplification product, wherein the amplification is simultaneously carried out in each of the reaction chambers; performing dHRM analysis of the amplification products in each of the reaction chambers to capture a melt curve signal, wherein the dHRM analysis is simultaneously carried out in each reaction chamber; and comparing the melt curve in each reaction chamber to a plurality of melt curves from known nucleic acid sequences using computer algorithms, thereby identifying and quantitating the microbial cells in the heterogeneous sample.

In one aspect of the present invention, the reaction mixture containing the intact microbial cells is loaded into 10,000 or greater reaction chambers. Those of skill in the art will appreciate that a number of different methods can be used to load the reaction mixture into the reaction chambers. In one embodiment, the reaction mixture is passively load using, for example, capillary forces to draw the reaction mixture into the chamber, but other methods, both active and passive, can be used to load the reaction mixture. Once loaded, the reaction mixture is subjected to cell lysis in situ (e.g., to release the nucleic acids contained in the microbes into the reaction mixture of each reaction chamber). Once released from the cell, the nucleic acid can be analyzed by amplification, and high resolution melt curves for each partition can be obtained. Additional phenotypic and genotypic profiling of microbial cells prior to or post cell lysis can be carried out. Such profiling analyses may include, but are not limited to, speciation via cell imaging and determination of resistance.

As explained herein, the present invention is directed to methods, systems, and devices to selectively enrich microbial cells from a sample and to use the intact microbial cells in place of the target nucleic acid in the reaction mixture for digital high-resolution melt (dHRM) analysis as described in PCT Publication No. WO2018.119443A1, the teachings of which are incorporated herein by reference in their entirety (hereinafter, "the '443 publication").

In a preferred embodiment, each reaction chamber is a fixed reaction chamber that can hold up to 1 nL of reaction mixture. The use of fixed reaction chambers allows for all reactions to be subjected to the same manipulation simultaneously or at the same time. This is in contrast to droplet-based embodiments, where droplets are generated and subjected to a thermal gradient and/or a chemical lysis step one droplet at a time, which can give rise to variations in reaction and/or analysis conditions. Partitioning the sample to be analyzed into 1 nL or smaller volume in fixed reaction chambers, which are manipulated simultaneously, allows for higher homogeneity across reaction chambers thereby reducing reaction-to-reaction variation. Further, fixed reaction chambers allow for the reaction mixture to be divided up into multiple non-targeted small volume reactions while avoiding the problem of contamination. In contrast, droplet-based methodologies require droplets with the captured cell target to be moved around after capture which not only increases the chance for loss of sample/droplets, but also increases the likelihood of cross-contamination between reaction chambers (see, e.g., Zhao, Yang and Krishnendu Chakrabarty, "Cross-contamination avoidance for droplet routing in digital microfluidic biochips." *IEEE Transactions on Computer-Aided Design of Integrated Circuits and Systems* 31.6 (2012): 817-830) In contrast, using fixed reaction chambers, these problems can be avoided because the capture and manipulation of the target cells are carried out in situ in a series of non-droplet partitions. When manipulating pathogenic microbes, droplet-based systems can generate aerosols, requiring the need for appropriate containment. This is not the case when using fixed reaction chambers, which minimize the need for containment. Thus, although droplets can be used in place of the fixed reaction chambers, many of the advantages achieved with the use of fixed reaction chambers are not seen when using the droplet-based method.

The methods, systems, and devices of the present invention, which employ the use of intact microbial cells, provide additional benefits over previously disclosed methods. The methods and systems of the present invention provide improved sensitivity by removing biases resulting from DNA extraction and by limiting the detection of human DNA and other contaminating DNA as well as carryover PCR inhibitors. Microfluidic chips limit the volume of reaction mixture to less than 20 thus the integration of DNA extraction with dHRM requires modification of standard extraction protocols that elute in 50-200 µL. This can lead to a biased loss in genomic DNA due to limitations in the ability to elute all pathogen DNA equally in such a small volume and may lead to an increase in DNA breakages. In contrast, isolation and concentration of intact viable microbial cells from blood components and non-clinically relevant microbial DNA (i) provides cleaner and more concentrated pathogen in a low volume sample, (ii) eliminates the competition for primers and dye by human DNA, allowing for more efficient PCR reactions, (iii) eliminates extraction bias, and (iv) shortens chip preparation time and costs.

In addition, the use of intact microbial cells in the methods and systems of the present invention provide provides opportunities for downstream phenotypic analysis. For instance, the methods of the present invention allow for broad-based pathogen detection with co-localization of resistance markers. This is in contrast to prior approaches involving the digitization of template genomic DNA that does not determine linkages between targets on the plasmid and genomic DNA from the same cell. Even when all the targets are present on the genomic DNA, linkages may not be observed due to chromosomal breakages during sample extraction and handling.[9] The methods and systems of the present invention, which use intact cells (microbial cells) as templates for each reaction chamber, provides the opportunity to profile targets from multiple target DNAs derived from a single microbial cell to determine multi-trait linkages. Thus, the methods and systems disclosed herein allow for the characterization of multisite diversity in a heterogeneous population. This is important for targeted treatment of poly-microbial infections displaying antibiotic resistance. For example, treatment of two concurrent pathogens that are individually resistant to different single antibiotics can be treated with the combination of those two antibiotics, while treatment of a single infectious strain resistant to the same two antibiotics would require a third option for treatment. Current dHRM methodologies cannot distinguish between these two scenarios, but the whole or entact-cell dHRM methodologies of the present invention can. Since patients can exhibit different tolerances or reactions to various antibiotics, the methods and systems of the present invention can provide a practitioner with more treatment options that would otherwise be overlooked.

Further, the methods and systems of the present invention provide improved quantification that accurately reflects cell count rather than the number of template DNA detected. With each reaction chamber of the chip representing a single cell, rather than a single piece of extracted DNA, quantification following identification reflects actual cell numbers. Unlike previous approaches, quantification of identified species using the methods disclosed herein is not biased by species-specific differences in genome copy number (ploidy bias) or by variations in target amplicon copy numbers in a single chromosome or DNA fragment.

Existing cell counters or similar technologies that manipulate single cells are generally geared towards eukaryotic cells that are larger in size and easier to lyse. Such technologies are also often expensive and based on size or fluorescence measures from single cells that require sophisticated instruments. They do not speciate or provide the ability to characterize the nucleic acid material for genotypic determination of traits such as resistance. Single cell sequencing platform provides promise; however, they often require a series of processes including purification of DNA and multiple steps for preparation of DNA for sequencing, which increases both the complexity and turnaround time. In contrast, the methods of the present invention are advantageous over these other methods because they carry out capture of microbial cells, lysis, amplification and characterization of its genetic material all within a single reaction well with one master mix or reaction mixture. Moreover, with the methods of the present invention, no upfront information regarding the target cell is required to partition the sample; with the methods of the present invention, the sample is partitioned (loaded) into the reaction chambers without the need to have information about the target cell. Prior to the present invention, there were no methods that had the capabilities to merge single whole-cell analysis, dPCR and precise ultrafast HRM.[10,11] The present invention addresses this need by providing the methods disclosed herein that can be used on, for example, a dHRM bench top, small-footprint (60 mm×40 mm), cost-effective platform device that allows for the reliable heating with simultaneous ultrafast high resolution imaging of, for example, 20,000 reaction wells on the microfluidic chip[12]. The optics employed in the system are able to sensitively capture sequence-defined loss in fluorescence melt curves from the extremely small picoliter volume reactions on the microfluidic chip. Clinically relevant bacterial loads are estimated to fall typically within the range of 1-1,000 cfu per 1 mL sample.[13,14] Thus, the systems of the present invention use a commercially available chip with 20,000 picoliter-scale reaction chambers, allowing for the loading of cells at a density of 1 target per 20 wells. This guarantees that 99.5% of positive wells will contain a single target (determined by Poisson distribution statistics).[15,16]

BRIEF DESCRIPTION OF THE DRAWINGS

The present application contains at least one drawing executed in color. Copies of this patent or patent application publication with color drawing(s) will be provided by the Office upon request and payment of the necessary fee.

DETAILED DESCRIPTION OF THE INVENTION

Figure 1:
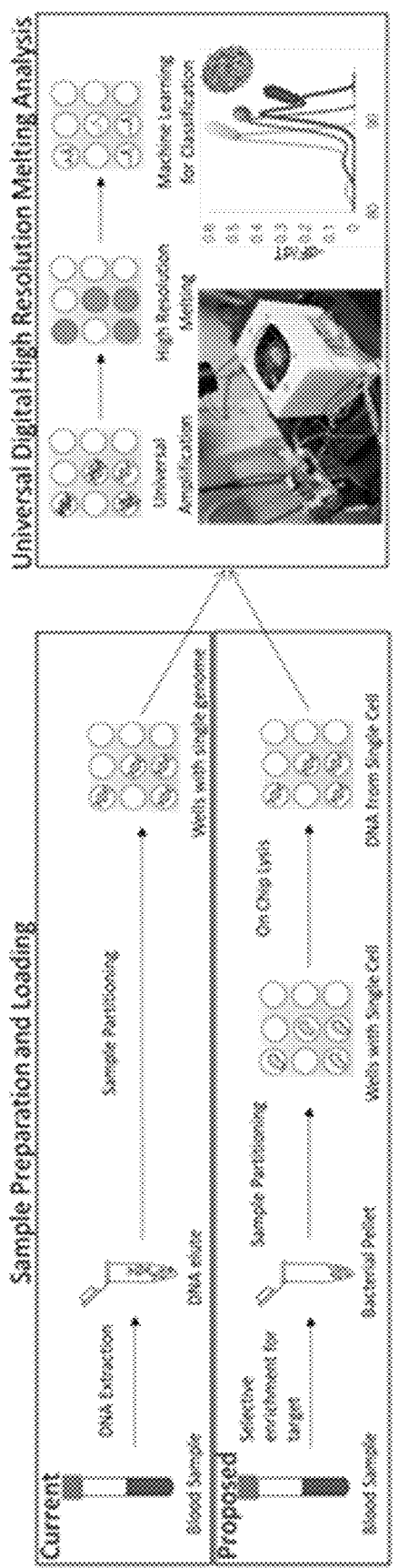
FIG. 1 is a schematic illustrating the methodological differences between the current (Top) dHRM methods as described in the '443 publication and the methods disclosed herein (Bottom). Both methodologies begin with the collection of a sample of interest. In the diagram, this is illustrated as a blood sample, but this illustration is not meant to limit the type of sample to be analyzed with this system. (Top left) According to the methods described in the '443 publication, the sample undergoes semi-automated DNA extraction. Target DNA is eluted into a small volume and loaded with dHRM reagents onto a dHRM device. One embodiment of the HRM device is illustrated in which the low volume elution sample is loaded into a chip-loading blade and partitioned into 20,000 picoliter reactions by dragging the blade across a micro-patterned surface. The chip is inserted into the dHRM device (Right) for thermal cycling, melt curve generation, and data processing. (Bottom) In the methods disclosed herein, DNA extraction and partitioning are advantageously replaced with sample preparation to enrich intact bacterial cells, partitioning of whole cells, and in-well lysis prior to amplification and dHRM analysis. This alternative enrichment and partitioning scheme enables single cells, rather than single genomes, to be partitioned across the device wells, which decreases the impact of host DNAs, enables accurate cell counts, and linkage between multiple HRM markers.
Figure 2:
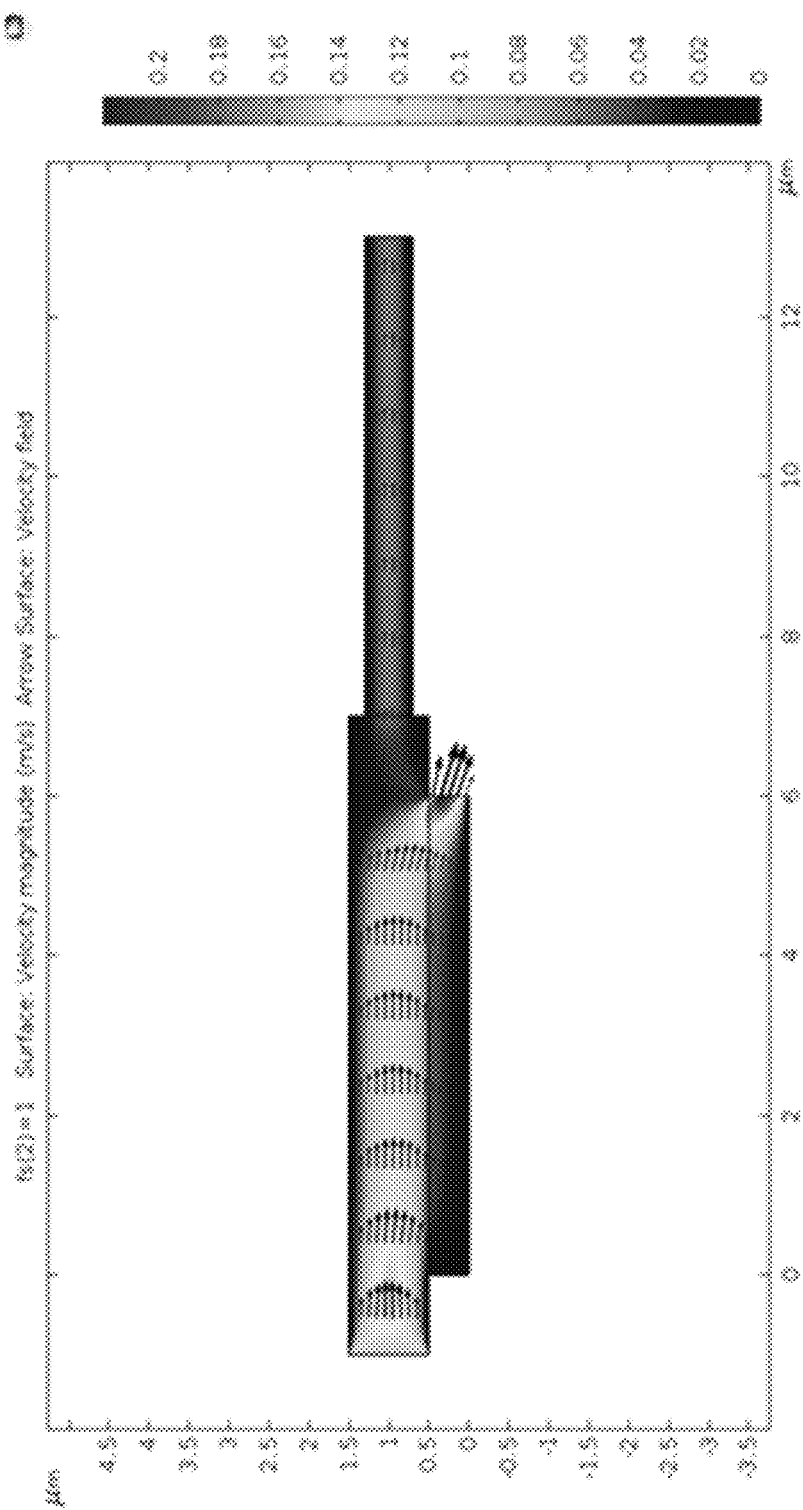
FIG. 2 describes the fluid velocity profile as it passes through the system. Along the membrane, the pathogens are blocked and carried forward by the plasma, whereas most of the plasma exits from the bottom channel.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety herein. In case of conflict, the present specification, including definitions, will control. Other features and advantages of the invention will be apparent from the following detailed description and figures, and from the claims.

The present invention is based, in part, on the development of an integrated platform enabling the enrichment of microbial cells from a sample; the mixing of this enriched sample with master mix to form a reaction mixture; the loading and partitioning of this reaction mixture into fixed reaction chambers, preferably on the platform of a dHRM device; the in situ lysis of the reaction mixture, i.e., the enriched sample of microbes that has been partitioned, to form a lysed sample in each of the reaction chambers; amplifying the lysed sample to generate an amplification product; performing dHRM analysis on the amplification product in each of the reaction chambers to generate a melt curve; and comparing the melt curve in each reaction chamber to a plurality of melt curves from known nucleic acid sequences using computer algorithms, thereby determining the sequence of target nucleic acid in each reaction chamber. The methods of the present invention uniquely combine partitioning individual microbial cells together with in situ lysis and dHRM analysis, which enables the identification and absolute quantification of multiple microbes in a poly-microbial sample. The unique combination of the enrichment of microbial cells from a sample with cell-based partitioning, in-situ lysis, amplification and dHRM methodologies lowers the limits of detection and enables detection of low-level microbial populations, while providing opportunities to interrogate phenotypic properties of viable microbial cells before genotypic analysis by dHRM.

In one aspect, the sample is selectively enriched for microbial cells and combined with a master mix to form a reaction mixture. As used herein, a master mix is used to refer to a mixture of the reagents needed to carry out the various steps of the methods disclosed herein. For instance, the master mix can include all of the reagents needed to carry out the lysis step, the amplification step, and the HRM analysis step. In addition, the master mix can include all of the reagents needed to carry out the phenotypic and/or genotypic profiling of the microbial cells prior to and/or post cell lysis. Such reagents include, but are not limited to, one or more primers, one or more DNA intercalating dye, one or more reference dye, a buffer, an enzyme, and one or more HRM reagents to form a reaction mixture.

The reaction mixture is then partitioned into 10,000 or greater reaction chambers using loading techniques known to and used by those of skill in the art. Once the reaction mixture is loaded in the reaction chambers, the microbial cells are lysed, and amplification is performed on each fixed reaction chamber to generate an amplification product for each chamber or partition. Following amplification, the nucleic acid sequences in the amplification product are detected by simultaneously heating and imaging the partitioned reactions, followed by melt curve analysis using machine learning.

In some embodiments, enrichment of the microbial cells is performed following a selective buffer-based lysis step of human and/or non-microbial cells and fragmentation of human chromosome and background DNA. That is to say, human and/or non-microbial cells and fragmented human chromosome and background DNA are first lysed in a selective buffer-based lysis step, and then the sample is enriched for the microbial cells. Any lysis buffer suitable for lysing human cells or any other non-microbial ells can be used in this step, provided there is no lysis of the target microbial cells. Further, there should be no carry-over of agents that inhibit amplification and HRM analysis methods. Suitable buffers for use in this step include, but are not limited to, osmotic lytic agents, such as deionized water, NaCl, $NH_4Cl^-$, $KHCO_3$, $NH_4Cl$ and/or detergent-based chaotropic buffers with an alkaline pH (pH 7.5 to 9 or above). In addition, any enzyme including, but not limited to, DNAse can be used to degrade background nucleic acid, including the nucleic acid released from the lysis of mammalian cells. This enrichment step can be manually done by the user or, alternatively, it can be done by using automated fluidic systems to lyse background cells and filter out the desired microbial cells.

Following the removal of human and/or non-microbial cells, fragmented human chromosome and background DNA, the sample is then enriched for cells containing microbes (e.g., white blood cells), followed by lysis of these cells to release microbial cells and, if needed, a second enrichment step for microbial cells can be performed as described above.

In some embodiments, enrichment is performed using a magnetic filtration. Magnetic filtration-based enrichment of the sample is carried out by the addition of a paramagnetic medium, by introduction of the mixture into a microfluidic flow-through-channel, or by micro-capillary interaction with a magnetic field, and then collecting the targets of interest and residual fluid via separate outlets. For instance, the microfluidic device might consist of one or more inlet channel (or inlets) and one or more outlet channels (or outlets). The sample introduced at the inlet is made to flow through the filtration region where the cells are diverted and from the initial flow path-lines. The target cells pass through the region to one of the outlets and are collected for further analysis. The other background cells are either localized in the filtration region or exit the system through outlets other than the target cells. The device may also include microchambers or pockets to isolate and capture background cells, while passing through the filtration region, whereas target cells flow in a fixed path and exit from the outlet. The device can have multiple regions of the filtration system with varying parameters of magnetic strength to have efficient target cell enrichment. Suitable paramagnetic media include, but are not limited to, gadolinium- and manganese-based agents, such as gadopentetate dimeglumine (gadolinium diethylene triamine pentaacetic acid (Gd-DTPA)), gadodiamide (gadolinium diethylene triamine pentaacetic acid bis-methylamide (GD-DTPA-BMA)), Gadoteridol (Gadolinium-1,4,7-tris (carboxymethyl)-10-(2' hydroxypropyl)-1, 4, 7-10-tetraazacyclododecane (Gd-HPD03A]), gadoterate meglumine (gadolinium-tetraazacyclododecane tetra acetic acid (Gd-DOTA), Dotarem, gadobenate dimeglumine; and gadobutrol. Suitable manganese-based agents include, but are not limited to, Mn-DPDP, ethylenediaminetetraacetic acid (Mn-EDTA), Pentamang diethylene triamine pentaacetic acid (Mn-DTPA).

In still other embodiments, enrichment is performed using a size-selective filter. In one such embodiment, the plasma is removed post-lysing of background human cells, and the sample volume is reduced by a cross flow filtration device. The lysing of background human cells is carried out as described above using, for example, osmotic lytic agents such as deionized water, NaCl, NH4Cl—KHCO3, NH4Cl and/or detergent based chaotropic buffers. The filtration is carried out by flowing sample comprising microbial cells in plasma through a microfluidic device consisting of two channels with a filter sandwiched between, adding several designs of resistance channel to the top channel, the fluid is forced to drain through the filter and to exit the device from the bottom channel, while the targets of interest and reduced sample volume flow through the top channel.

Once the sample is enriched, the enriched sample is combined with master mix which as described herein, includes, but it not limited to, a buffer, such as a high fidelity buffer, the reagents needed for microbial cell lysis, the regents needed for amplification, and the reagents needed for HRM analysis of the amplification product(s) or amplicon(s). The master mix includes at least one microbial cell lysing agent and at least one buffer suitable for dHRM. In some embodiments, the buffer is a high fidelity buffer. In some embodiments, buffer hydrophilicity is optimized by addition of detergents or surfactants to enable, for example, reliable loading of the master mix into the reaction chambers on the chip, such as a digital PCR chip. One or more detergents or surfactants can be present in the master mix at a concentration of from about 0.005% to about 0.85% v/v, or from about 0.01% to about 0.8% v/v. In an exemplary embodiments, from about 0.01% to about 0.8% v/v Brij L4 can be included in the master mix.

The reaction mixture, including the enriched sample, is then partitioned or fractionated into individual reaction chambers and, preferably, fixed reaction chambers. In this step, the reaction mixture is fractionated or partitioned into many small volume reactions, such that each reaction contains two or fewer target molecules, or one target molecule, or zero target molecules. Thus, following the amplification step, amplicons, i.e., amplification products, resulting from each reaction chamber will, in some cases, originate from two or fewer target microorganisms in the sample, less than two target microorganisms molecules in the sample, or one or fewer target microorganisms molecules in the sample. It will be appreciated by those of skill in the art that in view of ploidy, microorganism can exist as chains, with multiple cells being attached to one another and, thus, the target microorganism in a reaction chamber may include multiple cells. In some embodiments, partitioning the sample or reaction mixture includes partitioning or loading the sample or reaction mixture into at least 5,000 partitions in fixed reaction chambers. In some embodiments, partitioning the sample or reaction mixture includes partitioning the sample or reaction mixture into at least, 000 partitions in reaction chambers 10,000 partitions in fixed reaction chambers. In some embodiments, partitioning a sample or reaction mixture includes partitioning the sample or reaction mixture into at least 20,000, at least 50,000, at least 100,000, at least 200,000, at least 500,000, or at least 1,000,000 partitions in fixed reaction chambers.

In preferred embodiments, the reaction chambers are fixed reaction chambers. Each reaction chamber can have a volume of one nanoliter or less, one picoliter or less, or less than about one picoliter.

In some embodiments, the reaction mixture, which contains the enriched cells that have been combined or mixed with the master mix, is partitioned (or loaded) onto a microfluidic chip platform, including chips having an array of reaction chambers configured such that the reactions can fit into a single field of view for imaging. For example, in some embodiments, a dPCR chip may be used. Exemplary dPCR chips can include, for example, a silicon substrate etched with nano-scale or smaller reaction chambers. In some embodiments, the dPCR chip has a low thermal mass. For example, the chip may be constructed of thin, highly conductive materials that do not store heat energy. In some embodiments, a dPCR chip has a surface area of from about 50 mm$^2$ to about 150 mm$^2$. In some embodiments a dPCR chip has a surface area of about 100 mm$^2$. Limiting the surface area can allow for greater uniformity of heating of the chip during lysis, amplification, and melt analysis and a reduction in run-to-run variation in the melt cure analysis, a reduction in errors in melt curve generation, and increased discrimination of melt curves in the analysis. Chips useful in the methods and systems described herein include, for example, digital microfluidic chips, such as the chip sold by Thermo Fisher under.

Once the reaction mixture has been partitioned into the fixed reaction chambers on the chip, such as a dPCR chip, profiling of the microbial cells in the reaction mixture in each of the reaction chambers can be carried out using non-dHRM methods. Profiling of intact microbial cell in the reaction mixture using non-dHRM methods can optionally be performed prior to cell lysis. Suitable profiling methods include, but are not limited to, imaging of the intact microbial cell using chemical agents that include probes, light sensors, enzymes, etc., which are included in the master mix and combined with the enriched sample prior to loading or partitioning. In preferred embodiments, profiling of intact microbial cells in the reaction mixture is carried out prior to the lysis step using non-dHRM methods known to those of skill in the art.

In some embodiments, if a profiling step is to be carried out, a fluorescent sensor can be added to the reaction master mix to allow for the interrogation of phenotypic properties of viable microbial cells before genotypic analysis by dHRM. The fluorescent sensor emits a specific wavelength of light when encountering a resistant microbe. In some embodiments, the fluorescence sensor can be a FRET sensor that results in an increase in a fluorescent signal in the presence of the resistance. In some embodiments, the fluorescence activity of the sensor is correlated with resistance activity.

In some embodiments, if a profiling step is to be carried out, a florescent dye can be added to the master mix that that allows for cell counting and, in turn, cell quantitation. This can be accomplished by live/dead cell assay or by using DNA binding dyes that are cell permeable, such as, for example, STYO and SYBR, both of which are known to and used by those of skill in the art.

In some embodiments, if a profiling step is to be carried out after the lysis step, a protein assay can be used for colorimetric detection of genotypic properties such as resistance markets.

Following the profiling using non-dHRM methodologies, the microbial cells in each of the reaction chambers is carried out to create a lysed sample. In some embodiments, lysis of microbial cells is performed through a single heat step using a heating. Lysis can be carried out using chemical lysis, enzymatic lysis, thermal lysis, and combinations thereof. Suitable lysis buffers include (i) one or more non-ionic detergents including, but limited to, Triton-X 100, Tergitol, Nonidet P40, Dithiothreitol, and the like, and (ii) one or more stabilizing agents including, but not limited to, EDTA. Tris-phosphate k, glycerol, sodium azide, and the like, wherein the lysis buffer has an alkaline pH, such as a pH between 7.5-9.5. Other preferred lysis buffer include (i) one or more non-ionic detergents including, but limited to, Triton-X 100, Tergitol, Nonidet P40, Dithiothreitol, and the like, (ii) one or more stabilizing agents including, but not limited to, EDTA. Tris-phosphate k, glycerol, sodium azide, and the like, and (iii) YPER, wherein the lysis buffer has an alkaline pH, such as a pH between 7.5-9.5. In a preferred embodiment, the lysis buffer used is 25 mM Tris-phosphate (pH 7.8). 2 mM DTT, 2 mM 1,2-diaminocyclohexaneN,N,N',N'-tetraacetic acid, 10% glycerol, and 1% Triton® X-100. Any lysis agent(s) added to the reaction mix must ensure that lysis activity is initiated only after the cells are partitioned to ensure no loss of cells during preparation. In some embodiment, lysis agents used in the lysis step are heat activated.

Traditional thermal lysis methods are performed by heating the sample in a container using a heating device, such as a hot plate. This can be sometimes be long process, causing drying off of the moisture in the sample; however, the dHRM platform is ideally suitable to address this problem as evaporation is damped and significantly reduced by the sealing layer.

In another embodiment, lysis of the microbial cells is performed through a single heating step performed using the same system used for the amplification step and the step of detecting the amplified nucleic acid through digital high resolution melt analysis. Such a system can be similar to that described in in the '443 publication, but those of skill will appreciate that the system is not limited only to the system disclosed therein and variations of that system can be used.

In still another embodiments, lysis of microbial cells is performed through a series of rapid heating and cooling steps. The sample may be mixed with any lysis buffer suitable for use with a lysis method involving heat. Suitable lysis buffers include those lysis buffers described above. As with the heating method, lysis through a series of rapid heating and cooling steps can be carried out using the same heating system used for amplification and detection of the amplified nucleic acid by digital high resolution melt analysis. This system includes, but is not limited to, the system described in the '443 publication. Such a system can be similar to that described in the '443 publication, but those of skill will appreciate that the system is not limited only to the system disclosed therein and variations of that system can be used.

In some embodiments, lysis of microbial cells is performed through the addition of chemical agents similar to those added to the reaction mix described above. In some embodiments, lysis of microbial cells is performed by exposing the reaction chambers to an external electric field that creates a potential across the cell membrane causing lysis of the cells.

Complete microbial cell lysis is crucial for analyzing the DNA and RNA nucleic acid material of the microorganisms. For sensitive detection in samples with low copy number of targets, high lysis efficiency is needed. A combination of partitioning into small volume and digitization ensure high lysis efficiency. Digitizing cells in reaction chambers provides high surface area to volume for the lysing agent to act upon. Small volume reactions allow for the efficient transfer of heat to cells ensuring faster and more efficient lysis without affecting the integrity of the other reagents in the master mix, such as enzymes, and without interfering with the integrity of the released nucleic acid. Further, low number of cells per well advantageously results in a lower nucleic acid content to lower viscosity of the sample. Lowering the viscosity further increases lysis efficiency and also PCR efficiency in downstream steps. The lower amount of DNA provides lower viscosity for high amplification efficiency, enabling higher SNR for HRM analysis Once the microbial cells have been lysed, dHRM amplification, melting, and analysis is performed on the lysed sample using methodologies known to and used by those of skill in the art, such as those disclosed in the '443 publication, which is incorporated herein by reference in its entirety. The amplification is carried out using one or more amplification primers that generate amplicons from variable nucleic acid sequence regions present in a broad diversity of microbes. The resulting amplicons, when analyzed using dHRM, allow for the simultaneous detection, identification, and quantification of diverse microbes and their traits in a single assay. Exemplary amplification primers useful in the methods and systems described herein include bacterial primers, fungal primers, viral primers, and combinations thereof. Some examples of useful primers include, but are not limited to, primers targeting the bacterial 16S gene, Flavivirus NS1, NS3, NS5, and 3' NC gene regions, and fungal internal transcribed spacer 1 (ITS1), internal transcribed spacer 2 (ITS2), 5.8s rDNA, 18S, and 28S gene, coronavirus RdRP gene, ESBL gene regions may be targeted.

In some embodiments, combinations of at least two, at least three at least five, or at least ten unique amplification primers are used in carrying out the amplification reaction. In some embodiments, between two and six unique amplification primers can be used. In some embodiments, combinations of primers allow multiplexing for broad-based detection of multiple taxonomic units of organisms in a single sample.

In some embodiments, detection of bacterial, fungal, and viral pathogens can utilize different fluorescence channels. For example, a well-characterized universal fungal primer set targeting the ITS-1 region can be redesigned with a FRET quenched blue fluorophore (LUX primer technology, Thermo Fisher) such that upon incorporation into an amplicon, blue fluorescence will be generated. Similarly, a primer set targeting the HSV I and II DNA polymerase gene can be labeled with a Cy5 probe. Reactions positive for only green fluorescence can be analyzed according to the bacterial and resistance gene databases, while reactions positive for blue and green fluorescence will be identified as fungal and reactions positive for Cy5 fluorescence can be identified as HSV. Such multiplexed system can allow sorting of fungal and viral melt curves from bacterial and resistance melt curves, and can, in some embodiments, effectively triple the temperature range of melt curve output. In some multiplex embodiments, melt curve can be generated in a single fluorescence channel for all DNA, while fluorescence in other channels determines which database will be used for pathogen identification.

In some aspects, the amplification reactions described herein amplify an amplicon having a size greater than 500 base pairs, 750 base pairs, 1000 base pairs or 1500 base pairs in length. It is believed that an amplicon having a size greater than 500 base pairs, 750 base pairs, 1000 base pairs or 1500 base pairs in length allows for improved sequence discrimination and/or identification, thus minimizing background detection of degraded environmental/non-relevant DNA that is shorter in length and that was not removed during the enrichment step.

To carry out the amplification step, the amplification reagents must be present in the reaction chambers. As will be appreciated by those of skill in the art, the amplification reagents, and any other reagents needed to carry out the other steps, such as the high resolution melt, can be included in the reaction mixture. For example, any of the reagents or necessary reaction components described herein are added simultaneously in the master mix before partitioning.

As described elsewhere, the master mix is added to the enriched sample to form a reaction mixture. The master mix contains agents to enable loading, lysis, amplification, HRM analysis and optional non-dHRM profiling pre and post lysis. The reagents in the master mix must not interfere with any of the steps of the methods disclosed herein, and the lysis reagent(s) must not lysis the cells prior to partitioning or loading of the reaction mixture into the reaction chambers on the chip. Again, it has been determined that the methods of the present invention, which combine low cell count in each reaction chamber with small reaction volume in each reaction chamber, result in efficient lysis. Further, using digitized reaction chambers, complete lysis of the target cells in each reaction chamber releases a lower quantity of nucleic acid material, which is another advantage of the methods of the present invention. This is in contrast to other methods known in the art, where many cells are present in a reaction chamber, resulting in the release of higher amounts of material, providing a more viscous sample for high amplification efficiency.

For the amplification step, the master mix includes reagents needed for amplifying a target nucleic acid, such as one or more polymerases. In some embodiments, the polymerase is a high fidelity polymerase, including but not limited to, Q5, Platinum SuperFi II DNA Polymerase, and similar polymerases. The use of high fidelity polymerase can improve yield and allow for reduced reaction volumes, as well an ensure accuracy of amplification to result in more accurate melt curve analysis. To ensure high efficiency of lysis and removing background and PCR inhibitors by limiting dilution, reduced volumes of each reaction chamber is preferred. Use of a high fidelity enzyme is crucial to ensure high amplification efficiency, while allowing for high lysis efficiency and low interference from carry over inhibitors of the amplification enzyme resulting from mammalian cell lysis or released cell content.

The master mix can also include one or more buffers. In some embodiments, the buffer is a high fidelity buffer. In some embodiments, buffer hydrophilicity is optimized by addition of detergents or surfactants to enable reliable loading of master-mix into reactions on a digital PCR chip or in droplet digital PCR reactions. One or more detergents or surfactants can be present at a concentration of from about 0.005% to about 0.85% v/v, or from about 0.01% to about 0.8% v/v. In an exemplary embodiments, from about 0.01% to about 0.8% v/v Brij L4 can be included in the reaction mixture.

The master mix can also include one or more DNA intercalating dyes. During melt, the fluorescence of the DNA intercalating dye is lost as a function of temperature, allowing for imaging and measurement of the melt curve of the amplicon. In some embodiments, low-inhibitory DNA intercalating dyes can be used. For example, in some embodiments, EvaGreen dye (Biotium) can be included in the master mix. Other exemplary dyes useful in the methods and systems described herein include, but are not limited to, SYBR Green, Chai Green, LC Green, BoBo, ToTo, and the like.

In some embodiments, the master mix can include one or more reference dyes. Reference dyes are non-DNA-intercalating dyes that allow for excluding noise values in the melt curve analysis. In some embodiments, the reference dye is used to normalize the melt dye (DNA intercalating dye) at each temperature point. Any passive water soluble dye that does not interfere with PCR or melt analysis can be used. Some exemplary reference dyes useful in the methods and systems described herein include Tamra, TexasRed, AlexaFluor, Rox, and the like.

Figure 9:
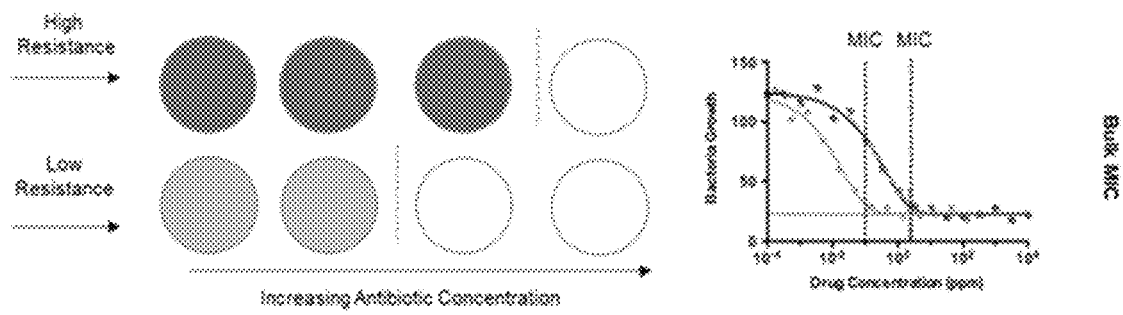
FIG. 9 shows a comparison of the method of the present invention (C) using single-cell sensor cleavage rate to other methods (A,B) relying on bulk culture antibiotic dilution series and single-cell antibiotic dilution series for quantitative determination of resistance including minimum inhibitory concentration for antimicrobial agent.
Figure 9:
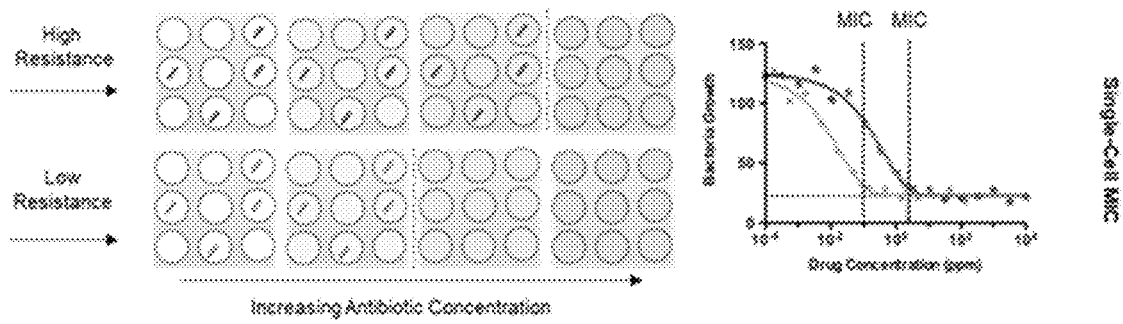
Figure 9:
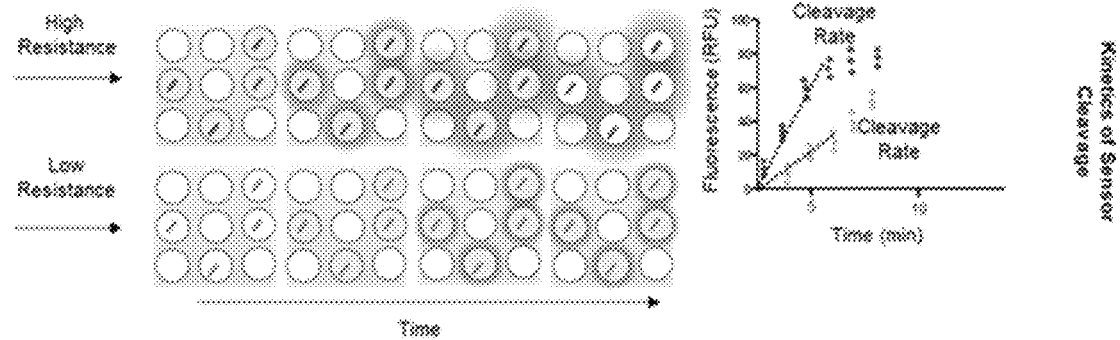

Once the amplification or universal PCR is complete, a melt analysis is conducted for all reactions simultaneously using the methodology and device described in the '443 publication. FIG. 9 of the '443 publication, together with the corresponding description in the specification, provides an exemplary integrated system that can be used to perform the melt analysis. Since each reaction amplifies from a single target molecule, each digital melt curve is a sequence fingerprint of only one sequence within a given heterogeneous sample. Some methods and systems useful for carrying out the melt analysis use an integrated dPCR chip, heating device, and imaging device.

In some embodiments, the reaction mixture can also include one or more reference dyes. Reference dyes are non-DNA-intercalating dyes that allow for excluding noise values in the melt curve analysis. In some embodiments, the reference dye is used to normalize the melt dye (DNA-intercalating dye) at each temperature point. Any passive water soluble dye that does not interfere with PCR or melt analysis can be used. Some exemplary reference dyes useful in the methods and systems described herein include, but are not limited to, Tamra, TexasRed, AlexaFluor, Rox, and the like.

In some embodiments, the imaging device is configured to simultaneously image in multiple light channels, while the reaction chambers are being heated. In some embodiments, the system can achieve multiple channel fluorescence (i.e., a two-channel fluorescence, a four-channel fluorescence, a six-channel fluorescence, etc.) necessary for bacterial, fungal, and viral detection in a simplified and rapidly-triggered optical configuration. In some embodiments, a motorized filter wheel may be used. In some embodiments, a filter slider can be used to host a single custom exciter-emitter filter cube, which can be multiband pass with a polychroic mirror (Chroma) to reflect 2, 3, 4, 5, 6, 10, or more excitation spectra and allow the respective number of emission spectra to pass through. For example, a custom filter slider can be used to enable simultaneous imaging of EvaGreen melt curves in FITC channel, ROX loading control in TRITC channel, and LUX primers in DAPI and Cy5 channels while avoiding slow motorization speeds of a filter wheel.

In some embodiments, the melt analysis can include controlling a temperature difference between any two points on the chip or platform during heating to 0.6° C. or less when performing melt analysis of the amplicon. In some embodiments, differences in the high temperature calibrator melt temperature on the chip or platform vary from 0.22° C. to 0.6° C., after excluding the outliers due to evaporation at the corners and edges of the chips or platforms. In some embodiments, with evaporation outliers included, median absolute deviation ranging from 0.05° C. to 0.1° C. and standard deviation of 0.06° C. to 0.13° C. occur across the chip or platform. As compared to conventional PCR, the smaller reaction volumes of dPCR could, in some embodiments, lead to larger variations in melt temperature (Tm) due to evaporation. However, in some embodiments, the small form factor of the digital chip or platform may maintain a more uniform thermal gradient across the chip or platform, leading to smaller variations in Tm. A previously published study reported Tm differences ranging from 0.35° C. to 1.24° C. across 32-96 well plate melt instruments with standard deviations of 0.018° C. to 0.274° C.[44] Performance could be improved by optimizing for loading errors and evaporation. For example, the application of oil onto the loaded reaction wells could be sensitive to timing and amount deposited, and automation would ensure that the corner wells are covered as quickly as the central wells to minimize evaporation.

In some embodiments, the heating of the dPCR chip is performed at a heating rate of from about 0.002° C./s to about 1° C./s or from about 0.005° C./s to about 0.5° C./s. The melt analysis of the amplicon can be performed by simultaneously heating and imaging the digital PCR chip is performed at a rate that is synchronized with the heating rate. For example, heating of the conductive block can be independently controlled by standalone software, while the proxy temperature measurement from the surrogate chip or platform can be synchronized with fluorescent imaging by the microscope control software (e.g., NIS-Elements). Synchronizing imaging with temperature measurement can be accomplished with, for example, the use of an NIS-Elements compatible temperature acquisition system (Tokai Hit Co., Japan) using a K-type thermocouple probe. However, in some instances, such acquisition systems only provide limited resolution of temperature measurement to 0.1° C. with a temperature sampling rate of ~0.2 Hz irrespective of the imaging rate. To compensate, the conductive block temperature can be precisely controlled, a repeatable relationship between the conductive block-embedded RTD and the surrogate chip-embedded or platform-embedded thermocouple established, and integrated thermocouple temperature data and fluorescence imaging data can be used to plot melting curves.

In some embodiments, the methods can further include performing automated melt curve classification with an analysis device having a processor configured to perform machine learning. The melt analysis of the amplicon can be performed, in some embodiments, by simultaneously heating and imaging the partitions to produce a melt curve for the amplicon. The method can include profiling the sequence of the target nucleic acid by comparing the melt curve for the amplicon to a plurality of melt curves from different nucleic acid sequences. The plurality of melt curves can include at least one reference melt curve from a known nucleic acid sequence. The method can include automated profiling of the sequence of a target nucleic acid by use of a computer model or algorithm that classifies the target nucleic acid based on the comparison to the reference melt curve. The computer model algorithm can be a machine learning algorithm for automated melt curve classification. In some embodiments, the machine learning classification algorithm can use a Naive Bayes classifier. In some embodiments, the method can include profiling the sequence of a target nucleic acid by using a Support Vector Machine (SVM). The method can include comparing the melt curve for the amplicon to a plurality of melt curves from different nucleic acid sequences to profile the sequence of a target nucleic acid. In some embodiments, the method can involve excluding melt curves below a threshold melt temperature to profile the sequence of a target nucleic acid. The method can include comparing melt curve shape or Tm of the amplicon. Probability based classification models useful in the methods and systems described herein include Gaussian Naïve Bayes (NB), multinomial Logistic regression (LR), and Multi-layer Perceptron (MLP) approaches for probabilistic classification. NB allows for incorporation of prior knowledge into the prediction model. For example, in some embodiments, epidemiological prevalence can be added as prior probabilities to provide added robustness of identification. Some embodiments can use equal priors, i.e. equiprobable organism classes.

In some embodiments, the algorithm can apply OVO SVM to match a test melt curve to a melt curve contained in a pre-defined database. In some embodiments, a pre-defined database can include melt curves of one or more typical pathogens, such as, for example, neonatal pathogens. In some embodiments, a melt curve anomaly detection algorithm using probabilistic classification is employed. Thus, training melt curves for each organism class can be used to build statistical models for those classes. Then the probability of a test curve belonging to each class can be calculated and this can be used as a measure for outlier detection. This approach is uniquely made possible by the novel high-throughput dHRM format described herein, where thousands of training curves are generated per run to robustly model each organism class.

Classification can, in some embodiments, be accomplished by combining the NB model with a decision rule to choose the most probable class as the label for a test curve using the maximum a posteriori (MAP) rule. In some embodiments, LR can be used to model the training data and compare classification performance to that of NB. LR model coefficients can be initially estimated using a squared regularizing function and then solved using maximum likelihood estimation. Goodness of fit can be measured by calculating the deviance of the model. In some embodiments, a non-linear MLP model can be constructed using the same training data and can have multiple layers of neurons that each use a non-linear logistic activation function. Back propagation can be used for training and can minimize the cross-entropy loss function to generate probability estimates for whether a test curve belongs to each organism class. The classification accuracy of each approach described above can be optimized with parameter tuning and tested using LOO, k-fold, and bootstrap cross validation on a given database of organisms. The best performer can be used to explore anomaly detection methods, such as for detecting unknown pathogens. In some anomaly detection embodiments, the Shannon entropy (SE) approach can be applied. The SE is a measure of the uncertainty in the posterior probabilities of a test curve, which can be calculated using the best performing probabilistic classification model described above. Higher magnitudes of SE are associated with more uncertainty in the classification decision made, which enables finding empirical thresholds on the entropy to minimize erroneous classifications. In some embodiments, this can enable the algorithm to abstain from making a decision for a classification with high associated entropy and instead provide information about how close to the current classes of pathogen that the curve is. At the same time, the SE can be used to generate a confidence score for all test curves, thus providing a more informative diagnostic answer. The databases of organisms can be segmented into training organisms and mock anomaly test organisms for this purpose and again LOO, k-fold, and bootstrap cross validation can be used to determine an optimal entropy threshold giving the highest accuracy in anomaly detection. In some embodiments, greater than 99% accuracy can be achieved in the identification of non-database organisms in mock anomaly datasets.

In some embodiments, dynamic temperature warping (DTW) can be used as a method to calculate a distance-from-class measure for outlier detection. DTW is typically a measure for estimating the similarity between two temporal sequences. In some embodiments of the system, temperature sequences can replace temporal sequences. By sweeping one melt curve over the other, DTW calculates the optimal match between the sequences, by trying to explain any fluctuations in the y-axis of melt curve by warping the temperature axis. A statistical model can then be built on the DTW measure for each class to identify melt curves with DTW measures that are unlikely, according to an empirically selected threshold that minimizes Type I and II errors. In some embodiments, information theoretic techniques can be used to estimate upper bounds on the number of pathogens that can be discerned.

In some embodiments, the method can further include calculating and/or assigning a confidence score or measure to the resultant classification. Thus, confidence of the determined melt curve classification can be provided and a determination can be made whether a given melt curve classification, for example a given species identification or sub species identification, can be determined to be clinically relevant.

In some embodiments, DTW can be applied first to identify any melt curves that are highly anomalous, followed by classification using LR or Multilayer Perceptron modeled on pre-defined database, then calculation of SE as a confidence measure on the prediction. In some embodiments, uncertainty in classification can be established using the LR model. In some embodiments, the Shannon entropy can be calculated across the posterior probabilities. Misclassified melt curves have a higher entropy in comparison to the correctly classified melt curves. Thus Shannon entropy measurement of the posterior probability can be used along with the prediction class as a measure of confidence of the classification.

In some embodiments, the method can further include subjecting the sample to a first heating rate to obtain a first melt curve signature; subjecting the sample to a second heating rate to obtain a second melt curve signature; and performing a heating rate-dependent melt curve analysis using a computer model or algorithm that classifies the target nucleic acid based on the comparison to the reference melt curve, such as by using a machine learning algorithm for automated melt curve classification. In some embodiments, subjecting the sample to a first heating rate and a second heating rate includes cooling the sample and re-melting the same sample. The number of re-melt cycles that can be performed can include, e.g., at least one re-melt cycle, at least two re-melt cycles, at least five re-melt cycles, ten or fewer re-melt cycles, five or fewer re-melt cycles, or two or fewer re-melt cycles. In some instances, the number of re-melt cycles that can be performed may be limited by photobleaching effects. In some embodiments, subjecting the sample to a first heating rate and a second heating rate includes subjecting a first portion of the sample to a first heating rate to obtain a first melt curve signature, and subjecting a second portion of the sample to a second heating rate to obtain a second melt curve signature. It has surprisingly been discovered that some nucleic acid molecules exhibit heating rate-dependent melt profiles and that the rate-dependent melt profiles can be used for more precise target identification. It was previously generally thought that heating rate changes only result in shifts in melt curve Tm, whereas the dynamic melting characteristics of a PCR product are thought to be primarily determined by GC content, sequence length, and nucleotide order.[44,45] However, the inventors have discovered that some long amplicons are highly sensitive to melting ramp rate, which not only shifts their Tm, but also changes the number and size of distinct melting transitions present. The ability of the methods and systems described herein to identify a heating rate dependence of melt curve shape is in large part due to the tunability, uniformity, and throughput of the digital melt platform. For the long amplicon sequences studied, slower heating rates resulted generally in a single melt transition, whereas faster rates generated multiple melting domains. The inventors have surprisingly discovered that this response to heating rate is highly sequence dependent. Some long amplicon sequences maintained the same melt curve shape for multiple heating rates, while others do not. Thus, the response of a long amplicon to heating rate changes provides additional sequence-specific information that could enhance the specificity of melt curve-based sequence profiling. That is, where one ramp rate cannot discriminate two sequences by their melt curve, a combination of multiple ramp rates may reveal distinct melt responses. Without wishing to be bound by theory, it is believed that the mechanism underlying these differences may involve kinetic sampling of transition states. For example, slower rates would be expected to enable amplicons to sample a wider range of transition states, where shifting, re-organized binding, or secondary structure formation could effectively average out the fluorescence decay across the bulk population of amplicons. Faster rates may induce more uniform transition behavior involving abrupt local DNA "bubbles" that melt separately at a different temperature than the remainder of the sequence. Indeed, faster rates of melting have previously been associated with higher Tm accuracy in homozygous melt analysis.[34] Alternatively, since heteroduplex melting has been found to be more apparent at faster heating rates, the multiple melt domains we observe at faster ramp rates may be the result of distinct heteroduplex binding transition states induced in homoduplex molecules.[34]

In some embodiments, amplification is performed post-cell lysis using methods that include endpoint PCR or isothermal amplification simultaneously with or post analysis by high resolution melting of each reaction partition. Isothermal amplification techniques may include, but are not limited to, techniques of Loop-mediated isothermal amplification (LAMP), Recombinase polymerase amplification (RPA).

In some embodiments, the chip holding the fixed-well reaction chambers might be packaged in a plastic or any other optically transparent material to enable the imaging of the dHRM process. The packaging can include fluidic components and channels to direct the sample and allow loading onto the chip.

In some embodiments, at least one of primers target >500 pb sequence. Capturing microbial cells, allows for the detection of only live or recently dead and intact cells. Use of with long amplicon further limits the amplification of background or contaminating nucleic acid.

The methods disclosed herein provide additional benefits, including limiting of contamination; reduction of bias due to extraction, handling, and amplification methods; the removal of endogenous inhibitors present in the sample that interfere with downstream amplification reactions; linkage analysis of multiple traits that may be on different DNA molecules or genomic fragments, but are present in the same cell and opportunities for profiling of intact microbial cells and their genomic DNA with non-dHRM methods in addition to dHRM.

EXAMPLES

The invention is further described in the following examples, which do not limit the scope of the invention described in the claims.

Example 1

Figure 3:
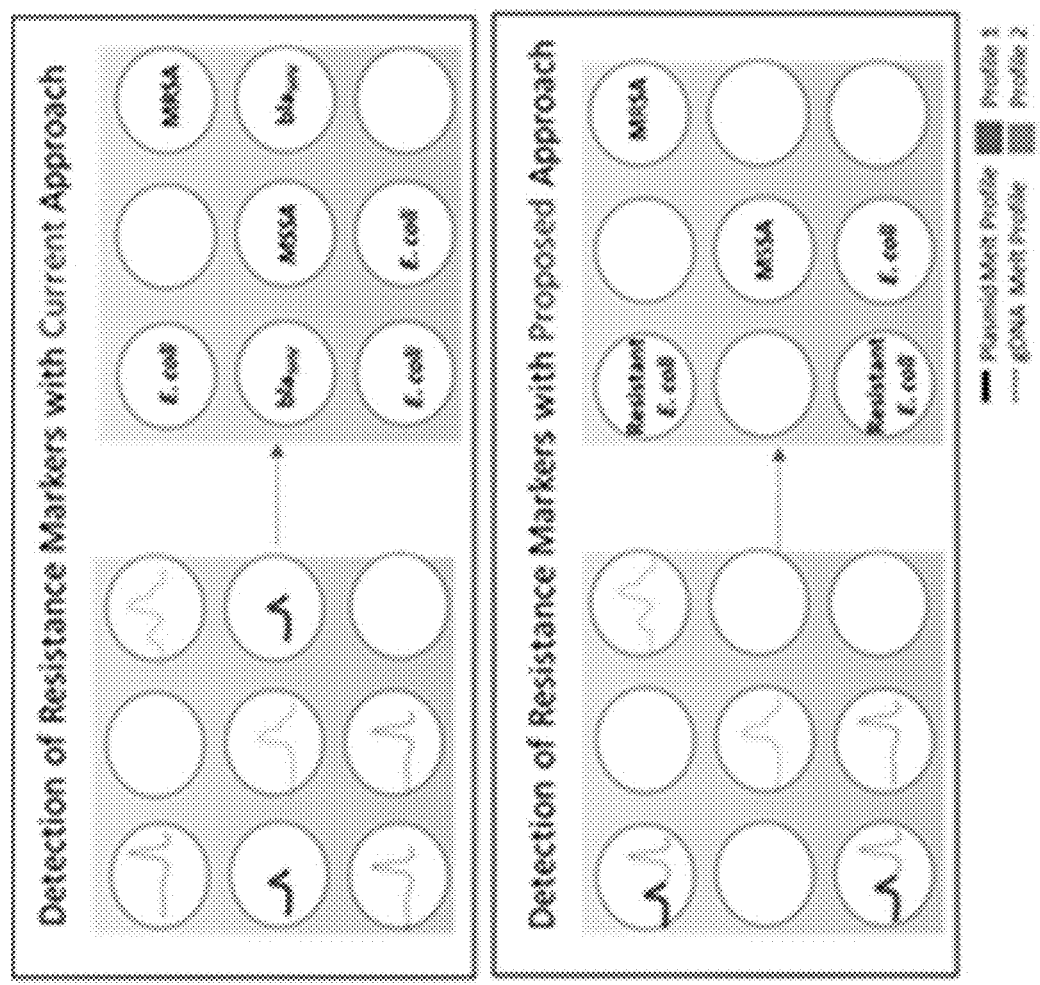
FIG. 3 is a schematic illustrating the differences in results that can be achieved between the current (Top) dHRM method as described in the '443 publication and the methods disclosed herein (Bottom) when the device is used to examine multiple markers, such as resistance and species markers. (Top) Resistance markers and species markers can be detected simultaneously using multiplexed primer sets using the system as described in the '443 publication. However, linkage between species and resistance markers is broken due to the DNA extraction process that is carried out in the method prior to partitioning, allowing for some wells to only exemplify the resistance marker, some wells to only exemplify the species marker, and few wells to exemplify both simultaneously. (Bottom) As a result of the methods of the present invention, wherein a reaction mixture containing enriched intact microbial cells is partitioned prior to in-well thermal lysis and dHRM analysis, multiple markers from the cell same are present in the same well, advantageously allowing for linkage to be established between these markers and those linkages to be quantified.

Single cell loading and PCR allows sensitive amplification of DNA from viable pathogens only at the single copy level, leading to the identification of low-level replicating and non-replicating bacteria in minimal blood sample volumes.[4,5] YFP expressing *E. coli* were used to test our ability to digitally load whole cells onto a microfluidic chip. An *E. coli* stock with an OD600-estimated 2,100 cells per chip-volume was loaded onto the microfluidic chip. 2,640 fluorescence-positive wells were counted on the chip, suggesting the presence of roughly 2,640 bacteria in the sample. This compared to a hemocytometer count of 2,700±75. Further, FIG. 3 shows the ability of the present invention to provide for polymicrobial quantification, where a mixture of YFP expressing *E. coli* and red-autofluorescent *Synechoccus* 28 *longates* cyanobacteria (for visualization) were loaded on to the chip. FIG. 3 illustrates ability of the methods of the present invention to detect pathogen with low abundance amongst another population with higher abundance. Previously, in the dPCR format, published data demonstrated the ability to digitally load multiple targets allowing for the recovery of pathogen ratios for quantification in polymicrobial samples with two pathogen DNAs, *S.* 29 *longates* and *L. monocytogenes*, in 1:1 and 1:3 ratios[6]. Further, thermal lysis shows comparable performance to standard lysis techniques used by diagnostic tests[7,8]. In results obtained, on-chip direct PCR from whole cells after an initial high temperature cycle yielded efficient on-chip lysis of *Escherichia coli* and PCR amplification. Lysis was confirmed by using propidium iodide to track the lysis of the membrane. Further, digital loading of single cells on the microfluidic chip allows for the profiling of microbial cells and their genomic DNA using non-dHRM methods to increase specificity of detection and to analyze traits that dHRM cannot provide information on in the current format with loading of isolated nucleic acid of interest. For example, as shown in FIG. 3, autofluorescent *Synechococcus* 29 *longates* cyanobacteria can be detected by capturing the signal in the red light channel, while GFP expressing *E. coli* can be detected by capturing the signal in another light channel. Imaging analysis upfront can be used to inform the settings for dHRM test run downstream or can be used in addition to the genotypic analysis performed by dHRM.

Example 2

A chip with 20,000 partitions, which is commercially available from ThermoFisher and is used for traditional dPCR, was used to establish the ability of the present invention to do on-chip lysis of *E. coli* cells followed by amplification and melting to generate melt curves from all reaction wells. *E. coli* cells were mixed with reagents including a cell lysis buffer and mastermix for lysis of the *E. coli* cells and subsequent amplification of DNA sequences within the 16S rRNA gene of the gDNA. This sample was then partitioned across the many picoliter scale reaction chambers and melt curves were simultaneously captured from all of the reaction chambers. FIG. 9 illustrates the successful lysis, amplification and capture of *E. coli* specific melt curves.

Example 3

Figure 4:
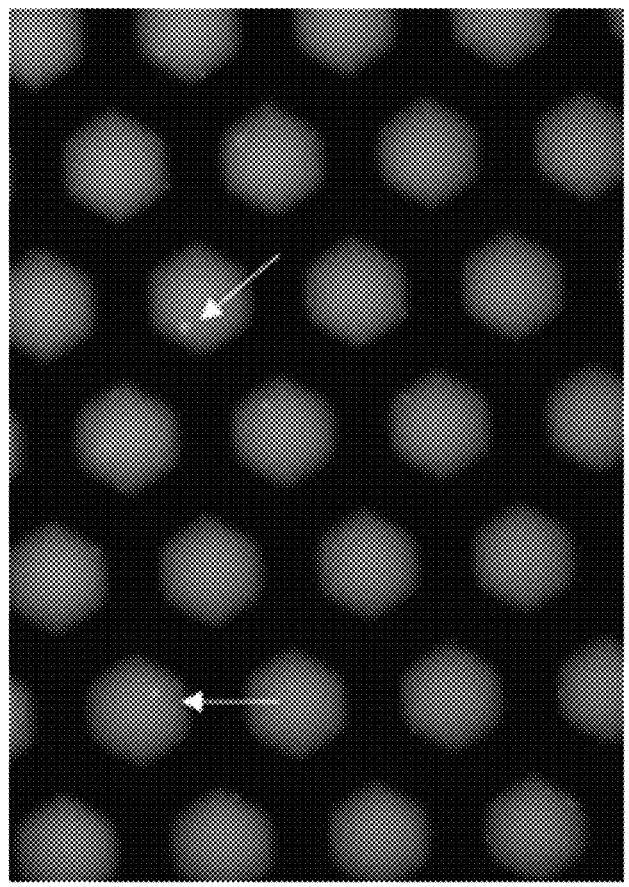
FIG. 4 provides illustrates the partitioning of individual cells into pico-liter-sized wells. In this method, cells were loaded onto a 20,000 well chip using a chip-loading blade. (Left) Figure shows a region of interest on the microfluidic chip loaded with a sample of yellow fluorescent protein (YFP)-expressing *Escherichia coli*. The arrow points to single *E. coli* cells (green dots) residing in individual wells. Circles highlight wells with more than one *E. coli* cell. (Right) An example of polymicrobial loading that is capable of partitioning a sample containing multiple species including the auto-fluorescent cyanobacteria *Synechococcus elongatus* (red) and YFP-expressing *E. coli* (green). Imaging alone of the intact, partitioned cells enables a rapid assessment of relative cell populations, with *S. elongatus* cells being much more prevalent that YFP-expressing *E. coli*.
Figure 4:
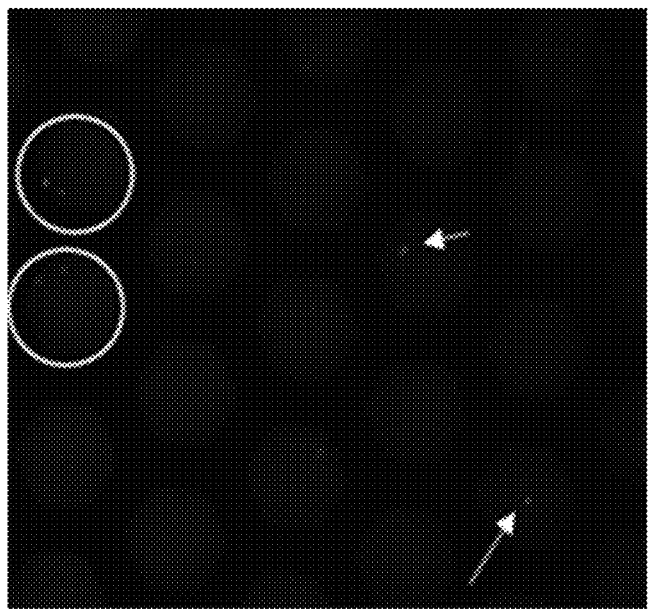
Figure 5:
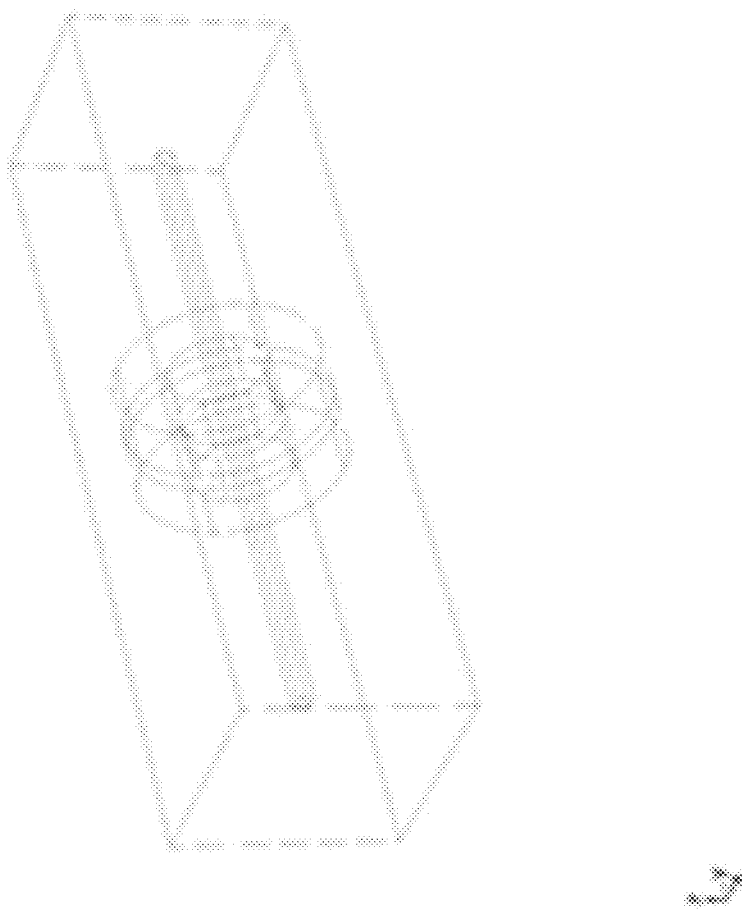
FIG. 5 illustrates a system containing N52 ring magnets where the magnet fields are aligned in the +y axis. The sample was collected in a fluidic channel aligned towards the center of the magnets. The surface magnetic flux density was set as ~0.35 T. The sample comprising whole blood and pathogens was introduced through the glass channel which was placed through the center of the coaxial magnets to filter the pathogens along with blood plasma while trapping the blood cells in the region between the magnets.
Figure 6:
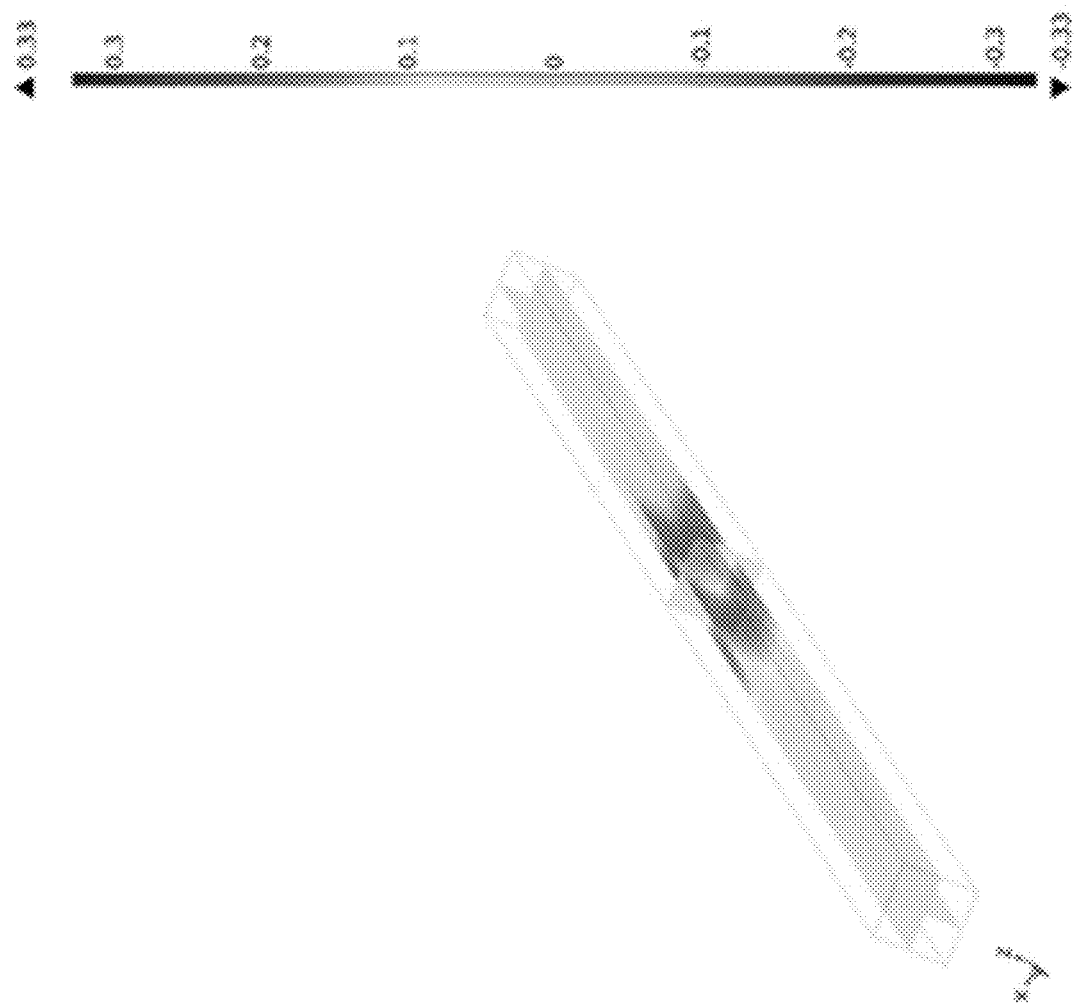
FIG. 6 illustrates the magnetic flux density (By) along the y axis based on the Magnetic Fields No Current (MFNC) module. ~0 T exists between the center of the 2 magnets where the blood components are filtered. The magnetic force is comparable to the applied hydrodynamic force such that the blood cells remain trapped in a region of low magnetic flux density while the smaller pathogens are filtered and reach the outlet along with the plasma.

A novel magnetic filtration technique was used to enrich pathogens for single cell digital high-resolution melting. Whole blood containing the pathogen was mixed with a paramagnetic medium to provide a highly paramagnetic environment to the predominantly diamagnetic cells and pathogens. The entire fluidic system was surrounded by permanent magnets possessing a ring configuration such that the magnetic field lines pass predominantly through the center of the ring. A finite element analysis (FEA) of this magnetic environment was simulated to optimize the concentration of the paramagnetic medium and to quantify the rate of deflection of the different hematocrit components when exposed to a high magnetic field. The entire setup was modelled as shown in FIG. 4. The ring magnets are aligned such that the like poles are facing towards each other. The magnetic flux density of the system was modelled to theoretically identify the magnetic minima (FIG. 5).

The magnetic flux density within the fluidic channel varies from +0.35 T to −0.35 T, and the signs are based on the vectorial directions of the magnetic flux densities. Between the magnets, there exists regions which are ~0 T that act as a capture point for the majority of the blood components.

The magnetic force experienced by the cells are described by the Equation 1, where $\aleph_s$ is the magnetic susceptibility of the cells, $\aleph_m$ is the magnetic susceptibility of the solution, V is the volume of the cell and the magnetic flux density and its gradient is described by $(B\rightarrow.\nabla)B\rightarrow$ and the magnetic permeability of free space is $\mu_0$ [1]:

$$F_{mag}\rightarrow = \frac{(\aleph_s - \aleph_m)V(B\rightarrow \cdot \nabla)B\rightarrow}{\mu_0}$$

The buoyancy force introduced by the surrounding medium provides the counter force to arrest the movement of the blood cells, Equation 2.

$$F_g\rightarrow = (\rho_s - \rho_m)Vg$$

The cell/sample of interest reaches equilibrium when:

$$F_{mag}\rightarrow + F_g\rightarrow = 0$$

The particle tracking module was used to simulate the cells of interest in a magnetic field environment.

A spherical particle representing RBC, WBC and a pathogen was modelled with densities of 1.090 g/cc, 1.070 g/cc and 1.116 g/cc based on the literature. The molar magnetic susceptibility of a Gadolinium-based paramagnetic medium is set as 0.3209*10^−3 L/mol.

In this instantiation, given a time period of 1200 seconds, pathogens such as *E. coli* do not have enough time to reach equilibrium and are therefore filtered out of whole blood along with the blood plasma.

Example 4

A physical device representing the simulation described in Example 3 was built. 1 mL of whole blood was mixed with a Gadolinium-based paramagnetic medium and spiked with fluorescent *E. coli*. The mixture was flown through a microfluidic channel surrounded by an assembly of ring magnets. The speed of the syringe pump was controlled to maintain a desirable flow rate of the sample between 5 µL/min to 30 µL/min. As the sample moved through the ring magnet assembly, the plasma with bacterial cell flowed through the microfluidic device and was collected at the end of the channel. The human cells did not have the time to flow through and remained in the microfluidic channel. The presence of *E. coli* in the filtrate was confirmed by fluorescence measurement which was significantly greater than the measurement of the filtrate from control sample. The control sample consisted of whole blood without any fluorescent *E. coli*.

Example 5

The cross filtration microfluidic device gets rid of the excess plasma (or elution buffer) volume from the sample, and thus the final volume obtained, is mixed with the master mix and served as an input to the microwell chip. The sample consisting of pathogens suspended in plasma or other elution buffer was introduced into the system. The device comprises two channels top and bottom hosting a membrane in between. The membrane pores are large enough to let the fluid pass through it, but small to allow the pathogen cells to pass through. The device has one inlet on the top channel and two outlets, both on the top and bottom. An additional channel can be added to the outlet of the top channel to add resistance to the sample flowing in the top channel, forcing most of the sample to go through the membrane and exit from the bottom to the waste reservoir. Simultaneously, the sample consisting of reduced fluid volume with the pathogen exited from the top channel and collected for the next step in the method. A finite element analysis (FEA) of the device was done to optimize the resistor channel dimensions to the top channel and determine the volume flow rate resulting at the top and bottom channel exits. The setup was modeled as illustrate in FIG. 1.

The Navier-Stokes equations describes the flow in the model of the free region and the Brinkman equations in the porous region. The porosity of the membrane was varied from 0.2-0.4. At the same time, the inlet velocity condition was varied between 0.02 m/s to 0.1 m/s. The outlets were fixed to 0 pa pressure conditions. The surface velocity profile was plotted for a stationary study to show that most of the sample (plasma only) prefers to pass through the membrane and drains through the exit, whereas some plasma carries the pathogens and exits from the top.

Example 6

Figure 7:
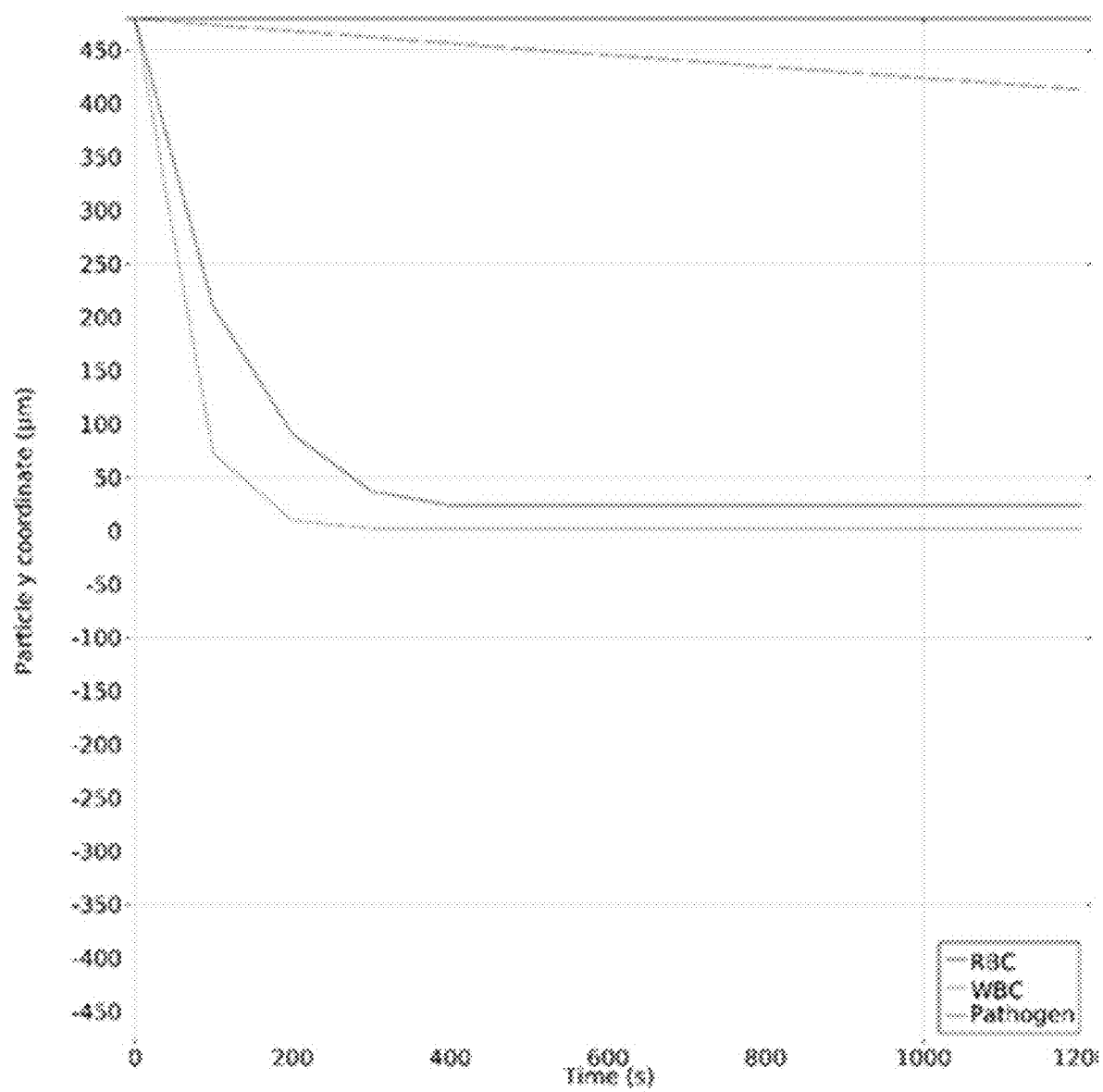
FIG. 7 demonstrates simulation of particle tracking of RBC, WBC and pathogens in a magnetic field. Based on the average sizes of the blood cells (RBC & WBCs), they reach equilibrium in terms of the applied hydrodynamic and magnetic force, in the region between the 2 ring magnets. However, owing to the small size of the pathogens, the hydrodynamic force overcomes the applied magnetic field to push them towards the exit port of the fluidic channel.
Figure 8:
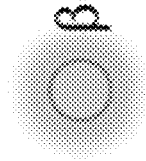
FIG. 8 illustrates single-cell loading and single-cell phenotypic resistance detection. Resistant (RFP and b-lactamase expressing) and non-resistant (GFP expressing) *E. coli* is mixed together and loaded on-chip along with enzyme activity sensor. Cleavage of the sensor by enzyme corresponds to blue fluorescence throughout a well. Only wells containing RFP expressing cells should give off significant blue sensor fluorescence.
Figure 8:
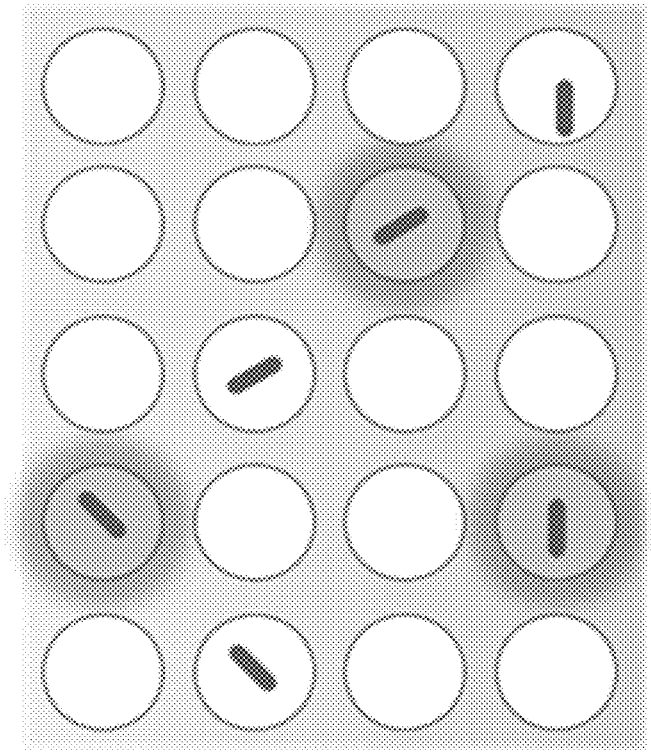

FIG. 7 illustrates the ability of the methods and systems disclosed herein to determine antimicrobial resistance using phenotypic detection prior to cell lysis based on incorporation of a fluorescent sensor that emits specific wavelength of light when encountering a resistant microbe. Here, *E. coli* resistant to ß-lactams is present in a mixed population containing both resistant and non-resistance *E. coli*. FIG. 8 demonstrates the quantitative determination antimicrobial resistance including determination of minimum inhibitory concentration for antimicrobial based on enzyme activity.

Example 7

Figure 10:
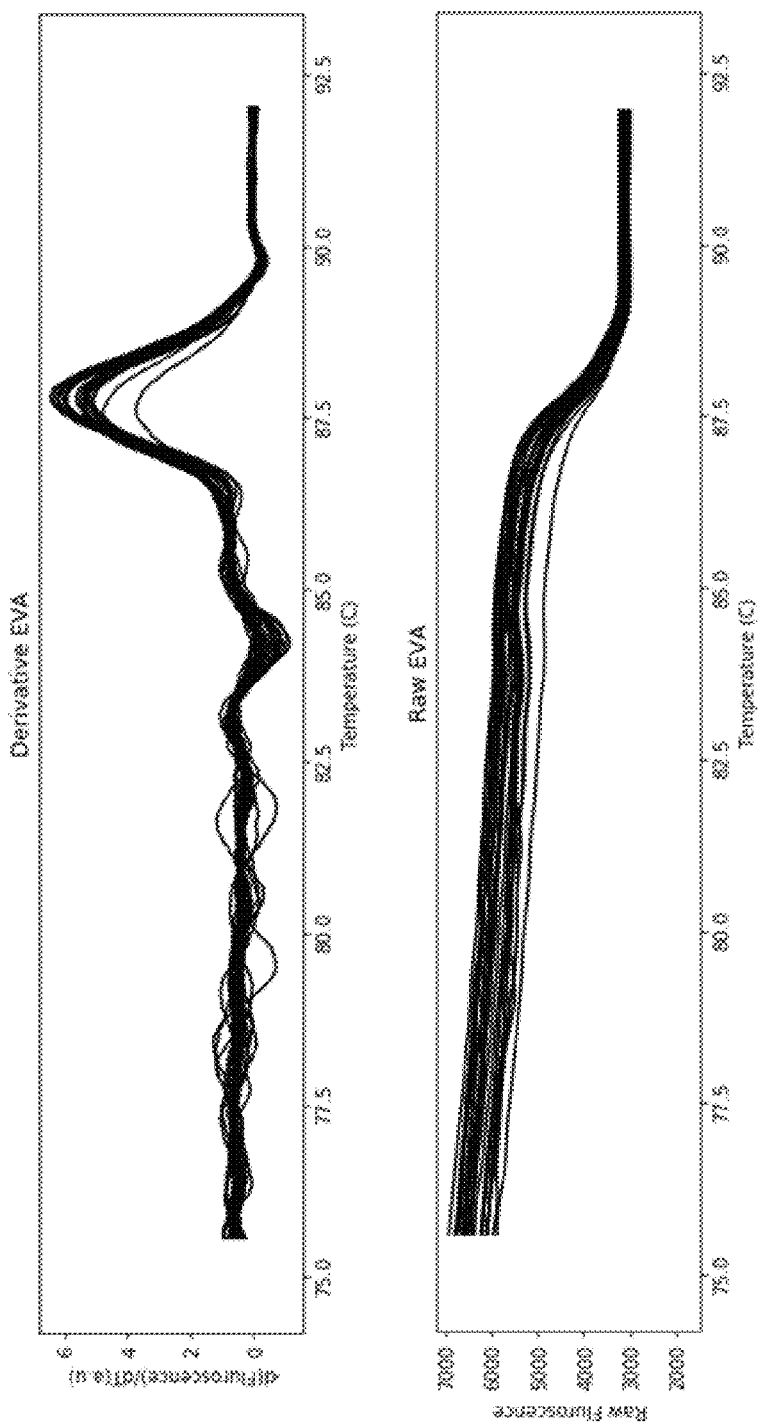
FIG. 10 illustrates melt curves representative of 16S amplicon of the *E. coli* DNA. These melt curves were generated by direct loading of cells onto a microfluidic chip, followed by on-chip amplification and melting.

FIG. 10 shows the amplification of target DNA sequences from both genomic and plasmid DNA directly from *E. coli* cells. *E. coli* cells were mixed with reagents including a cell lysis buffer and mastermix for lysis of the *E. coli* cells and subsequent amplification of DNA sequences within the 16S rRNA gene of the genomic DNA and antibiotic resistance gene within the plasmid DNA. As shown in FIG. 10 melt curves for both targets on plasmid DNA and genomic DNA are captured from the same reaction well.

Example 8

Figure 11:
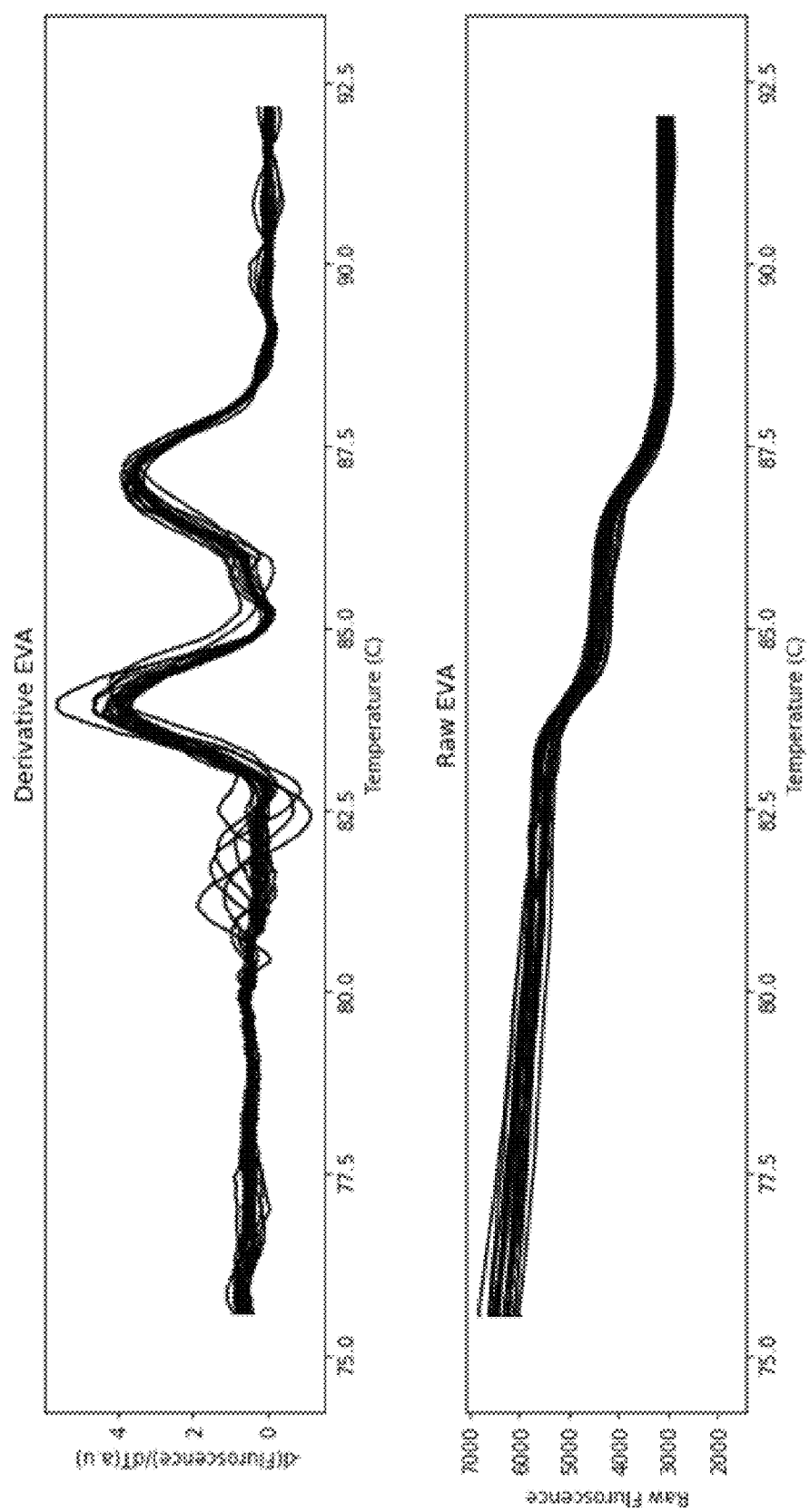
FIG. 11 illustrates melt curves that are representative of Km resistance markers and 16S amplicon of the *E. coli* DNA. Melt Curves for both targets on plasmid DNA and genomic DNA are captured from the same reaction well.

FIG. 11 shows amplification of target RNA sequences from Human Coronavirus Species.

REFERENCES

1. Frey, K. G. et al. Comparison of three next-generation sequencing platforms for metagenomic sequencing and identification of pathogens in blood. *BMC Genomics* 15, 96 (2014).
2. Prachayangprecha, S. et al. Exploring the Potential of Next-Generation Sequencing in Detection of Respiratory Viruses. *J. Clin. Microbiol.* 52, 3722-3730 (2014).
3. Sinha, M. et al. Emerging Technologies for Molecular Diagnosis of Sepsis. *Clin. Microbiol. Rev.* 31, e00089-17 (2018).
4. Bhat, S., Herrmann, J., Armishaw, P., Corbisier, P. & Emslie, K. R. Single molecule detection in nanofluidic digital array enables accurate measurement of DNA copy number. *Anal. Bioanal. Chem.* 394, 457-467 (2009).
5. Hindson, B. J. et al. High-throughput droplet digital PCR system for absolute quantitation of DNA copy number. *Anal. Chem.* 83, 8604-8610 (2011).
6. Velez, D. O. et al. Massively parallel digital high resolution melt for rapid and absolutely quantitative sequence profiling. *Sci. Rep.* 7,42326 (2017).
7. Boardman, A. K., Campbell, J., Wirz, H., Sharon, A. & Sauer-Budge, A. F. Rapid microbial sample preparation from blood using a novel concentration device. *PLoS One* 10, e0116837 (2015).
8. Gole, J. et al. Massively parallel polymerase cloning and genome sequencing of single cells using nanoliter microwells. *Nat. Biotechnol.* 31, 1126-1132 (2013).
9. Malentacchi, F. et al. Influence of pre-analytical procedures on genomic DNA integrity in blood samples: The SPIDIA experience. *Clin. Chim. Acta* 440, 205-210 (2015).
10. Baker, M. Digital PCR hits its stride. *Nat Meth* 9, 541-544 (2012).
11. Sedlak, R. H. & Jerome, K. R. Viral diagnostics in the era of digital polymerase chain reaction. *Diagn. Microbiol. Infect. Dis.* 75, 1-4 (2013).
12. Sinha, M., Mack, H., Coleman, T. P. & Fraley, S. I. A High-Resolution Digital DNA Melting Platform for Robust Sequence Profiling and Enhanced Genotype Discrimination. *SLAS Technol. Transl. Life Sci. Innov.* 247263031876984 (2018). doi:10.1177/2472630318769846
13. Kellogg, J. A. et al. Frequency of low level bacteremia in infants from birth to two months of age. *Pediatr. Infect. Dis. J.* 16, 381-5 (1997).
14. Dietzman, D. E., Fischer, G. W. & Schoenknecht, F. D. Neonatal *Escherichia coli* septicemia—bacterial counts in blood. *J. Pediatr.* 85, 128-130 (1974).
15. Dube, S., Qin, J. & Ramakrishnan, R. Mathematical analysis of copy number variation in a DNA sample using digital PCR on a nanofluidic device. *PLoS One* 3, e2876 (2008).
16. Vogelstein, B. & Kinzler, K. W. Digital Pcr. *Proc. Natl. Acad. Sci.* 96, 9236-9241 (1999).

What is claimed is:

1. A method for identification and quantification of microbial cells in a heterogenous sample, the method comprising:
    enriching the sample for microbial cells by removing non-microbial cells and nucleic acid from the heterogeneous sample to provide an enriched sample;
    combining the enriched sample with a master mix to form a reaction mixture, wherein the master mix comprises at least one microbial cell lysis agent and at least one reaction buffer for amplification and high resolution melt (HRM) analysis;
    partitioning the reaction mixture into at least 10,000 reaction chambers;
    lysing the microbial cells in the reaction mixture in each of the reaction chambers to create a lysed sample comprising a nucleic acid;
    performing amplification of the nucleic acid in the lysed sample in each of the reaction chambers to produce an amplification product, wherein the amplification is simultaneously carried out in each of the reaction chambers;
    performing digital HRM (dHRM) analysis of the amplification products in each of the reaction chambers to capture a melt curve signal, wherein the dHRM analysis is simultaneously carried out in each reaction chamber; and
    comparing the melt curve in each reaction chamber to a plurality of melt curves from known nucleic acid sequences using computer algorithms, thereby identifying and quantitating the microbial cells in the heterogeneous sample.

2. The method of claim 1, wherein the sample is enriched for microbial cells by removing non-target cells using a lysate buffer having a pH>9.

3. The method of claim 1, wherein the sample is enriched for microbial cells by removing non-target nucleic acid material using a DNAse enzyme.

4. The method of claim 1, wherein the sample is enriched for microbial cells by removing mammalian cells using a magnetic or magneto-densitometric separation column.

5. The method of claim 1, wherein the sample of microbial cells is enriched by size separation.

6. The method of claim 1, wherein the sample is enriched for microbial cells by removing non-target cells using a lysate buffer with a pH>9, and wherein the sample is concentrated to reduce volume of the enriched sample.

7. The method of claim 1, wherein the the amplification is carried out using polymerase chain reaction (PCR).

8. The method of claim 1, wherein the the amplification is carried out using endpoint PCR.

9. The method of claim 1, wherein the the amplification is carried out using isothermal amplification.

10. The method of claim 1, further comprising profiling of intact microbial cells in the sample prior to lysis using non-dHRM based analysis.

11. The method of claim 9, wherein the non-dHRM based analysis is performed on intact microbial cells in the sample using a light sensor, a probe, a stain, or a combination thereof.

12. The method of claim 10, wherein the non-dHRM based analysis is performed on intact microbial cells in in the sample by using a fluorescence resonance energy transfer (FRET) sensor for determination of antibiotic resistance.

13. The method of claim 1, further comprising performing genotypic profiling using non-dHRM methods.

14. A method for identification and quantification of microbial cells in a heterogenous sample, the method comprising:
    enriching the sample for microbial cells by removing non-microbial cells and nucleic acid from the heterogeneous sample to provide an enriched sample;
    combining the enriched sample with a master mix to form a reaction mixture, wherein the master mix comprises at least one microbial cell lysis agent and at least one reaction buffer for amplification and high resolution melt (HRM) analysis;
    partitioning the reaction mixture into at least 10,000 reaction chambers;
    profiling of the intact microbial cells in each of the reaction chambers using non-digital HRM (non-dHRM) based analysis;
    lysing the microbial cells in the reaction mixture in each of the reaction chambers to create a lysed sample comprising a nucleic acid;
    profiling of the lysed sample mixture in each of the reaction chambers using non-dHRM based analysis;
    performing amplification of the nucleic acid in the lysed sample in each of the reaction chambers to produce an amplification product, wherein the amplification is simultaneously carried out in each of the reaction chambers;
    performing dHRM analysis of the amplification products in each of the reaction chambers to capture a melt curve signal, wherein the dHRM analysis is simultaneously carried out in each reaction chamber; and
    comparing the melt curve in each reaction chamber to a plurality of melt curves from known nucleic acid sequences using computer algorithms, thereby identifying and quantitating the microbial cells in the heterogeneous sample.

15. The method of claim 14, wherein the sample is enriched for microbial cells by removing non-target cells using a lysate buffer having a pH>9, by removing non-target nucleic acid material using a DNAse enzyme, by removing mammalian cells using a magnetic or magneto-densitometric separation column, or by using a size-selective filter size separation.

16. The method of claim 14, wherein the sample is enriched for microbial cells by removing non-target cells using a lysate buffer with a pH>9, and wherein the sample is concentrated to reduce volume of the enriched sample.

17. The method of claim 14, wherein the the amplification is carried out using polymerase chain reaction (PCR), end-point PCR, or isothermal amplification.

18. The method of claim 14, wherein non-dHRM based analysis is performed on intact microbial cells in the sample using a light sensor, a probe, a stain, or a combination thereof.

19. The method of claim 14, wherein non-dHRM based analysis is performed on intact microbial cells in the sample by using a fluorescence resonance energy transfer (FRET) FRET sensor for determination of antibiotic resistance.

20. A method for identification and quantification of microbial cells in a heterogenous sample, the method comprising using a device comprising:
    an inlet to introduce the reaction mixture
    a fluidic enclosure housing a plurality of reaction chambers,
    a fluid path connecting the inlet and the plurality of reaction chambers arranged in the fluid path, such that each reaction chamber is capable of untargeted capture of at least one microbial cell comprising nucleic acid, and
    wherein the method comprises the steps of:
        introducing the sample into the device via the inlet, the reaction mixture sample comprising enriched microbial cells;
        flowing the fluid sample in the fluid path from the fluid inlet to the plurality of reaction chambers;
        lysing microbial cells in each of the plurality of reaction chambers to create a lysed sample;
        performing amplification on the sample simultaneously in all of the plurality of reaction chambers,
        performing digital HRM (dHRM) analysis on the sample simultaneously in all of the plurality of reaction chambers, to capture a melt curve from each reaction chamber; and
        comparing the melt curve in each reaction chamber to a plurality of melt curves from known nucleic acid sequences using computer algorithms, thereby identifying and quantitating the microbial cells in the heterogeneous sample.

* * * * *